(12) United States Patent
Iga et al.

(10) Patent No.: US 6,322,550 B2
(45) Date of Patent: Nov. 27, 2001

(54) METHOD FOR TRANSDERMAL ADMINISTRATION OF GP IIB/IIIA ANTAGONIST

(75) Inventors: Katsumi Iga, Osaka; Yukihiro Matsumoto; Shigeo Yanai, both of Hyogo, all of (JP)

(73) Assignee: Hisamitsu Pharmaceutical Co., Inc., Saga (JP)

(*) Notice: Subject to any disclaimer, the term of this patent is extended or adjusted under 35 U.S.C. 154(b) by 0 days.

(21) Appl. No.: 09/291,386

(22) Filed: Apr. 14, 1999

(30) Foreign Application Priority Data

Apr. 14, 1998 (JP) .................................................. 10-102521

(51) Int. Cl.⁷ ....................................................... A61N 1/30
(52) U.S. Cl. ............................................. 604/501; 604/20
(58) Field of Search ........................................ 604/501, 20

(56) References Cited

U.S. PATENT DOCUMENTS 5,983,130 * 11/1999 Phipps et al. .

FOREIGN PATENT DOCUMENTS

| 732121 | 9/1996 | (EP) . |
| 747092 | 12/1996 | (EP) . |
| 748636 | 12/1996 | (EP) . |
| 64-11564 | 1/1989 | (JP) . |
| 64-11565 | 1/1989 | (JP) . |
| WO96/33982 | 10/1996 | (WO) . |
| WO97/48395 | 12/1997 | (WO) . |
| WO97/48443 | 12/1997 | (WO) . |
| WO97/48444 | 12/1997 | (WO) . |
| WO97/49382 | 12/1997 | (WO) . |

* cited by examiner

*Primary Examiner*—Mark Bockelman
(74) *Attorney, Agent, or Firm*—Wenderoth, Lind & Ponack, L.L.P.

(57) ABSTRACT

A method for transdermal administration of a GP IIb/IIIa antagonist by iontophoresis, comprising plural electric current application steps, progressively reduced in current density. The method insures excellent pharmacologic efficacy with a low risk for side effects in the prevention and therapy of (1) angina pectoris, (2) unstable angina and (3) ischemic complications and coronary arterial reocclusion or restenosis associated with PTCA or coronary thrombolysis.

14 Claims, 5 Drawing Sheets

METHOD FOR TRANSDERMAL ADMINISTRATION OF GP IIB/IIIA ANTAGONIST

TECHNICAL FIELD

The present invention relates to a method for transdermal administration of a GP IIb/IIIa antagonist by iontophoresis, comprising plural electric current application steps, progressively reduced in current density.

BACKGROUND ART

In recent years a variety of compounds designed to produce antithrombotic effects through the inhibition of platelet aggregation by competitive antagonism against GP IIb/IIIa, one of the platelet receptors, have been synthesized for possible application to the prophylaxis and therapy of (1) angina pectoris, (2) unstable angina and (3) reobstruction and restenosis of coronary arteries after PTCA (percutaneous transluminal coronary angioplasty) or coronary thrombolysis, among other applications. Particularly among GP IIb/IIIa antagonists comprising 2-piperazinone-1-acetic acid derivatives, compounds having high antiplatelet aggregation activity have been discovered (e.g. JP-A-25285/1994, JP-A-316059). However, generally the following three problems have been pointed out with GP IIb/IIIa antagonist in common. The first problem is that the serum concentration threshold causing a prolongation of bleeding time, a side effect, is so close to the effective serum concentration range producing the main pharmacological efficacy that the serum concentration of the drug must be somehow controlled so that the main effect may be isolated from the side effect. The second problem is that therapeutic efficacy is not shown without maintenance of pharmacologically effective serum concentration for a long term (e.g. about not less than 3 days, preferably about 3 to 100 days, more preferably about 7 to 100, further more preferably about 7 to 30 days, most preferably about 7 to 14 days), in view of the operation mechanism of GP IIb/IIIa antagonists. The third problem is that because of the high hydrophilicity and poor mucosal penetration efficiency of those compounds, their application by the oral route, which is of convenience in self-administration, cannot be expected so that generally intravenous infusion, which is feasible only on an inpatient basis, has so far been the exclusive method of administration which is safe and effective.

The first and second problems suggest that the preferred serum concentration pattern of any GP IIb/IIIa antagonist is such that the drug reaches its therapeutically effective concentration range quickly and maintains that concentration range for a long time.

With regard to the third problem, nasal administration or transpulmonary administration, together with an absorption promoter, may be considered possible as a method enabling self-administration but is not satisfactory in that a transient excessive elevation of serum concentration in an initial phase following administration, which is observed with those administration methods in common, contributes to side effects. Transdermal administration may be mentioned as another method permitting self-administration but, as far as the conventional transdermal delivery system is concerned, the absorbability of those highly water-soluble compounds is generally very low even when they are formulated with an absorption promoter and other additives so that it cannot be considered to be a realistically useful method of administration. Supposing that the necessary absorption could be attained by some means or other, the absorption lag time would be too long (generally after application, it takes about a few hours for the drug to enter the circulation), thus failing to provide an ideal mode of administration.

Meanwhile, iontophoresis as a means for assisted transdermal absorption of drugs, by which the drugs are forced to penetrate the skin under the influence of an electrical energy, has been known for many years [Journal of Controlled Release, 18, 1992, pp.213–220; Advanced Drug Delivery Review, 9, 1992, p.119; Pharmaceutical Research, 3, 1986, pp.318–326]. This system is based on the principle that when a positively charged water-soluble compound, for instance, is incorporated in an anode patch to be affixed to the skin and an electric current is applied, the positively charged compound is forced, by electrical repulsion, to penetrate the stratum corneum of the skin, which is inherently impermeable, and get absorbed systemically. This system is currently applied to the self-administration of basic peptides such as calcitonin and parathyroid hormone and many techniques for efficient transdermal penetration have also been proposed (JP-A-16535/1994 and JP-A-103494/1997). Regarding the transdermal administration of a GP IIb/IIIa antagonist by iontophoresis, relevant disclosures can be found in WO 97/49382, WO 97/48395, WO 97/49382, JP-A-103494/1997 and JP-A-56827/1997. However, no sufficient studies have been undertaken on the optimum conditions of electrical current application for the administration of a GP IIb/IIIa antagonist by iontophoresis.

BRIEF DESCRIPTION OF THE DRAWINGS

FIG. 2 is a cross sectional view illustrating a patch exemplifying one of patches for the present invention used, wherein 1 shows an electrode, 2 shows a conductive layer, 3 shows a support, 4 shows an adhesion part, 5 shows a porous membrane.

FIG. 3. is a graph illustrating the change of the serum concentration of the compound obtained in Production Example 1 as time passed in Reference Examples 1, 2 and 3, wherein -■- shows the serum concentration of Reference Example 1, - ▲-shows the serum concentration of Reference Example 2, -●- shows the serum concentration of Reference Example 3.

DISCLOSURE OF INVENTION

Figure 1:
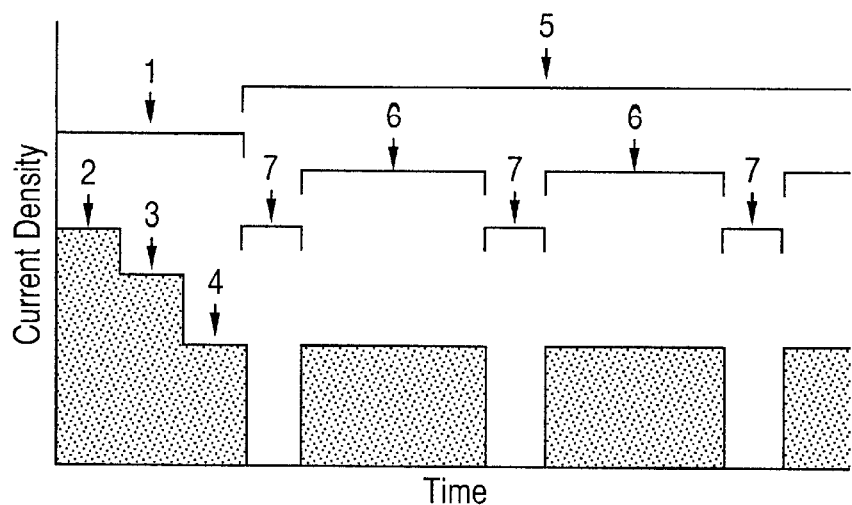
FIGS. 1-1 to 1-3 are examples of the electric current application status in the present invention, wherein 1 shows a first series of plural electric current application steps, 2 shows an initial current application step, 3 shows the second current application step, 4 shows the last current application step, 5 shows a further series of current application, 6 shows current applications in the further series, 7 shows intervals of non-electric current application.

The present invention provides a method for transdermal administration of GP IIb/IIIa antagonist by iontophoresis, which method stably maintains the effective serum concentration for a long term, insures expression of excellent pharmacological efficacy with a reduced risk for side effects, and can provide an opportunity of self-administration, in the prophylaxis or therapy of (1) angina pectoris, (2) unstable angina, and (3) reobstruction and restenosis of coronary arteries after PTCA (percutaneous transluminal coronary angioplasty) or coronary thrombolysis.

In the course of studying the methods for transdermal administration of a GP IIb/IIIa antagonist by iontophoresis, the inventors found that the control of the electric current application condition had an important role. As a result of further studies based on such finding, they invented the methods for transdermal administration of a GP IIb/IIIa antagonist by iontophoresis, having almost no side effect and performing excellent pharmaceutical efficacy, for treatment or prophylaxis of diseases such as (1) angina pectoris, (2) unstable angina or (3) reobstruction and restenosis of coronary arteries after PTCA (percutaneous transluminal coronary angioplasty). The methods comprise plural electric current application steps, progressively reduced in current density; or comprise the plural electric current application steps, progressively reduced in current density, followed by further series of electric current applications sufficient to maintain pharmacologically effective serum concentration. And, after further studies, the present invention has been completed.

Therefore, the present invention relates to (1) a method for transdermal administration of a GP IIb/IIIa antagonist by iontophoresis, comprising plural electric current application steps, progressively reduced in current density;

(2) the method in (1), which comprises two electric current application steps, progressively reduced in current density;

(3) the method in (1), wherein the current density of the initial electric current application step is about 0.005 to 0.5 mA/cm$^2$;

(4) the method in (1), wherein the period of the initial electric current application step is about 1 to 240 minutes.

(5) the method in (1), wherein the current density of the last electric current application step is about 10 to 80% of that of the initial electric current application step;

(6) the method in (1), wherein the period of the last electric current application step is about 1 minute to about 72 hours;

(7) the method in (1), wherein a GP IIb/IIIa antagonist is a compound of the formula:

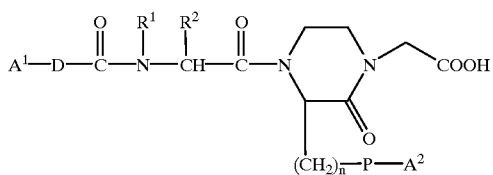

(I)

wherein $A^1$ and $A^2$ independently are a proton-accepting group;

D is a spacer having a 2- to 6-atom chain optionally bonded through a hetero-atom and/or a 5- or 6-membered ring which is, depending on its bonding position, counted as 2- or 3-atom chain;

$R^1$ is a hydrogen atom or a hydrocarbon group;

$R^2$ is a hydrogen atom or a residual group formed by removing —CH(NH$_2$)COOH from an α-amino acid, or $R^1$ and $R^2$ may be combined to form a 5- or 6-membered ring;

P is a spacer having a 1- to 10-atom chain optionally bonded through a hetero-atom and/or a 5- or 6-membered ring, provided that the 5- or 6-membered ring is, depending on its bonding position, counted as 2- or 3-atom chain; and n is an integer of 0 to 8, or a salt thereof;

(8) the method in (7), wherein $A^1$ and $A^2$ are independently an unsubstituted amino, amidino or guanidino group;

(9) the method in (7), wherein $R^1$ is hydrogen atom;

(10) the method in (1), wherein a GP IIb/IIIa antagonist is (S)-4-(4-guanidinobenzoylamino)acetyl-3-[3-(4-guanidinobenzoylamino)propyl]-2-oxopiperazine-1-acetic acid or a salt thereof;

(11) a method for transdermal administration of a GP IIb/IIIa antagonist by iontophoresis, comprising plural electric current application steps, progressively reduced in current density, followed by further series of electric current application(s) sufficient to maintain pharmacologically effective GP IIb/IIIa antagonist concentration in the serum;

(12) the method in (11), wherein the further series comprises about 2 to 99 subsequent electric current applications;

(13) the method in (11), wherein there is an interval of non-electric current application before each electric current application of the further series;

(14) the method in (13), wherein the interval of non-electric current application is about 0.1 to 120 minutes;

(15) the method in (11), wherein the current density of the further series of electric current applications is substantially the same as that of the last application step of the first series of electric current applications;

(16) the method in (11), wherein the absorption rate of the GP IIb/IIIa antagonist is about 0.01 to 50 mg/hour;

(17) a method for transdermal administration of a GP IIb/IIIa antagonist by iontophoresis, wherein the antagonist concentration in the serum is maintained at about 10 to 500 ng/ml, within about 240 minutes from initial electric current application step.

In the present specification, it should be understood that the codes with respect to amino acids, peptides and so forth as used in the present specification are based on codes according to IUPAC-IUB Commission on Biochemical Nomenclature, or conventional codes used in the field of art. When there are optical isomers for an amino acid, the amino acid represents an L-form, otherwise specifically defined.

The plurality of current application steps in the present invention means the number of current application steps per administration, which is preferably 2 to 10, more preferably 2 to 6, further more preferably 2 to 4, and most preferably 2 to 3. The current application steps are either serial "with a temporal interval" between the steps or serial "without a temporal interval". Preferably, those current application steps are continuous, without a temporal interval, while the electric current density is varied in the steps.

The current density for the initial current application step is generally about 0.005 to 0.5 mA/cm$^2$, preferably about 0.01 to 0.5 mA/cm$^2$, more preferably about 0.05 to 0.3 mA/cm$^2$. The current density for the next current application step immediately following the initial step, that is to say the second current application step, is not particularly restricted provided that it is lower than the current density used in the initial step. However, in case the second current application step is the last step, the current density for this step is preferably about 10 to 80%, more preferably about 20 to 60%, of the current density used in the initial step. In case the second current application step is not the last current application step, the current application can be repeated in one or more steps on condition that the current density in each step is lower than the current density in the immediately preceding step. It is so arranged that, as the result of such serial current application, the current density in the last current application step will be equal to about 10 to 80%, preferably about 20 to 60%, of the current density in the initial current application step.

The current application time for the initial current application step can be selected according to the current density used but is for example about 1 to 240 minutes, preferably about 1 to 120 minutes, more preferably about 30 to 120 minutes. The current application time for the subsequent step or steps, i.e. the second and subsequent current application steps, is not particularly restricted but is for example about 1 minute to 72 hours, preferably about 1 minute to 36 hours, more preferably about 1 minute to 24 hours, further more preferably about 2 to 24 hours, most preferably about 20 to 24 hours. Consequently, the current application time of this series including initial, second and subsequent steps is totally in a range of about 4 to 72 hours, preferably about 10 to 36 hours, more preferably about 20 to 24 hours.

The type of electric current for use in said current application is not particularly restricted but may for example be a direct current (DC) or a pulse direct current as used in the technology disclosed in JP-A-317997/1996, although the use of a pulse DC is preferred. The frequency of such a pulse current can be properly selected from the range of preferably about 0.1 to 200 kHz, more preferably about 1 to 100 kHz, further more preferably about 5 to 80 kHz. The ON/OFF ratio of said pulse current can be judiciously selected from the range of preferably about 1/100 to 20/1, more preferably about 1/50 to 15/1, still more preferably about 1/30 to 10/1.

More particularly, the frequency and ON/OFF ratio of the pulse current may be 30 kHz and 30% duty cycle [equivalent to the ON/OFF rate of 3/7] or 50 kHz and 50% duty cycle [equivalent to the ON/OFF rate of 1/1].

Voltage charged in each electric current application step is selected in any range of which voltage does not injure the skin of a live body and does not disadvantage the rate of transdermal absorption of a drug. The range is, for example, from about 0.5 to 30 V, preferably from about 2 to 20 V, more preferably from about 5 to 10 V.

Further, the present invention provides a method for transdermal administration of a GP IIb/IIIa antagonist by iontophoresis which comprises the first series of plural electric current application steps, progressively reduced in current density, followed by further series of electric current application steps sufficient to maintain pharmacologically effective serum concentration. The electric current application in the further series can be applied preferably about 2 to 99 times repeatedly more, preferably about 6 to 99 times, further more preferably about 6 to 13 times. Time period of one electric current application in the further series is not limited as long as the transdermal administration is effective. For example, the time period can be about one minute to 72 hours, preferably about one minute to 36 hours, more preferably about one minute to 24 hours, further more preferably about 2 to 24 hours, and most preferably about 20 to 24 hours.

The kind of electric current in the further series is exemplified as the same as in the above-mentioned first series. Voltage charged in each electric current application of the further series is exemplified as the same as that of each electric current application step of the first series, which is mentioned above.

The further series of electric current applications includes a single electric current application or plural electric current applications. In either case, an interval is preferably set just before each electric current application. The interval means a period in that electric current is not applied. An interval period is preferably about 0.1 to 120 minutes, more preferably about 0.5 to 120 minutes, further more preferably about 0.5 to 60 minutes. The first series of plural electric current application steps is recognized as one application, since the electric current is essentially continuously applied although the electric current density is varied in the first series period. The electric current application is repeated preferably about three to 100 times including the first series more preferably about 7 to 100 times, most preferably about 7 to 14 times. In the present invention, each one application including the first series is carried out preferably for one day-administration of GP IIb/IIIa antagonist. Therefore, the administration period of a GP IIb/IIIa antagonist, including the first and the further series, is preferably about three to 100 days, more preferably about 7 to 100 days, further more preferably about 7to 30days, most preferably about 7 to 14days. Each day-administration of a GP IIb/IIIa antagonist is preferably performed by exchanging the device, or anode patch and/or cathode patch, as mentioned below every administration.

Figures 1, 2:
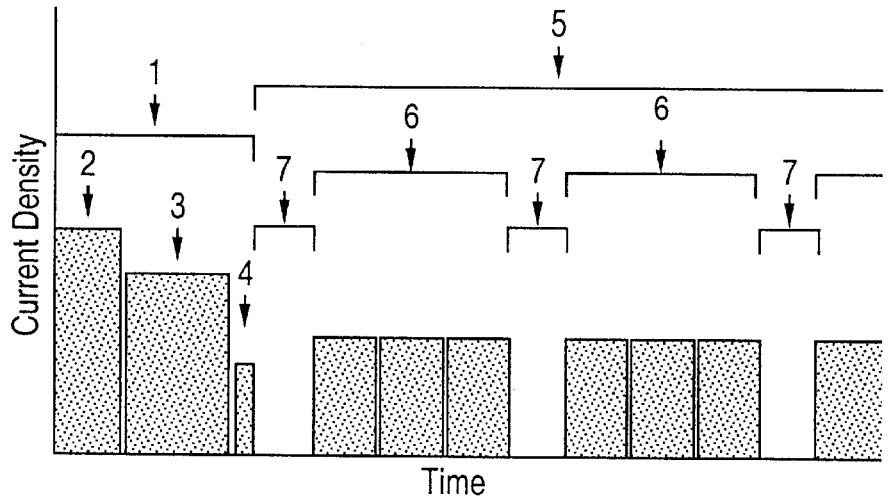
Figures 1, 2, 3:
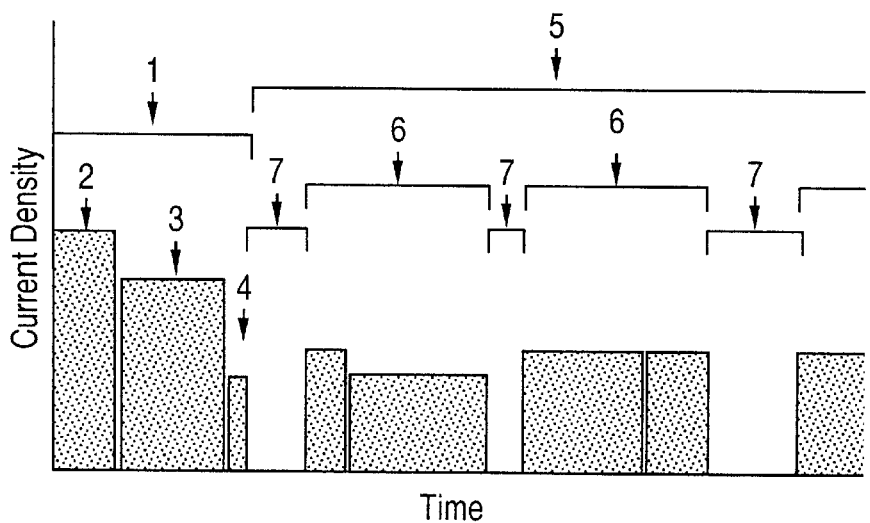
Figure 2:
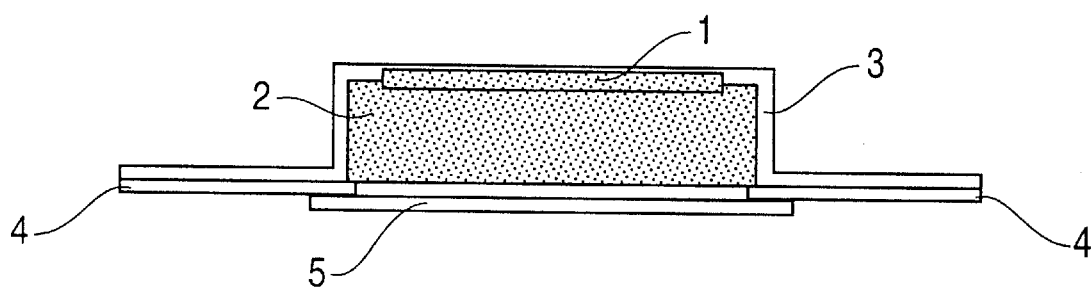
Figure 3:
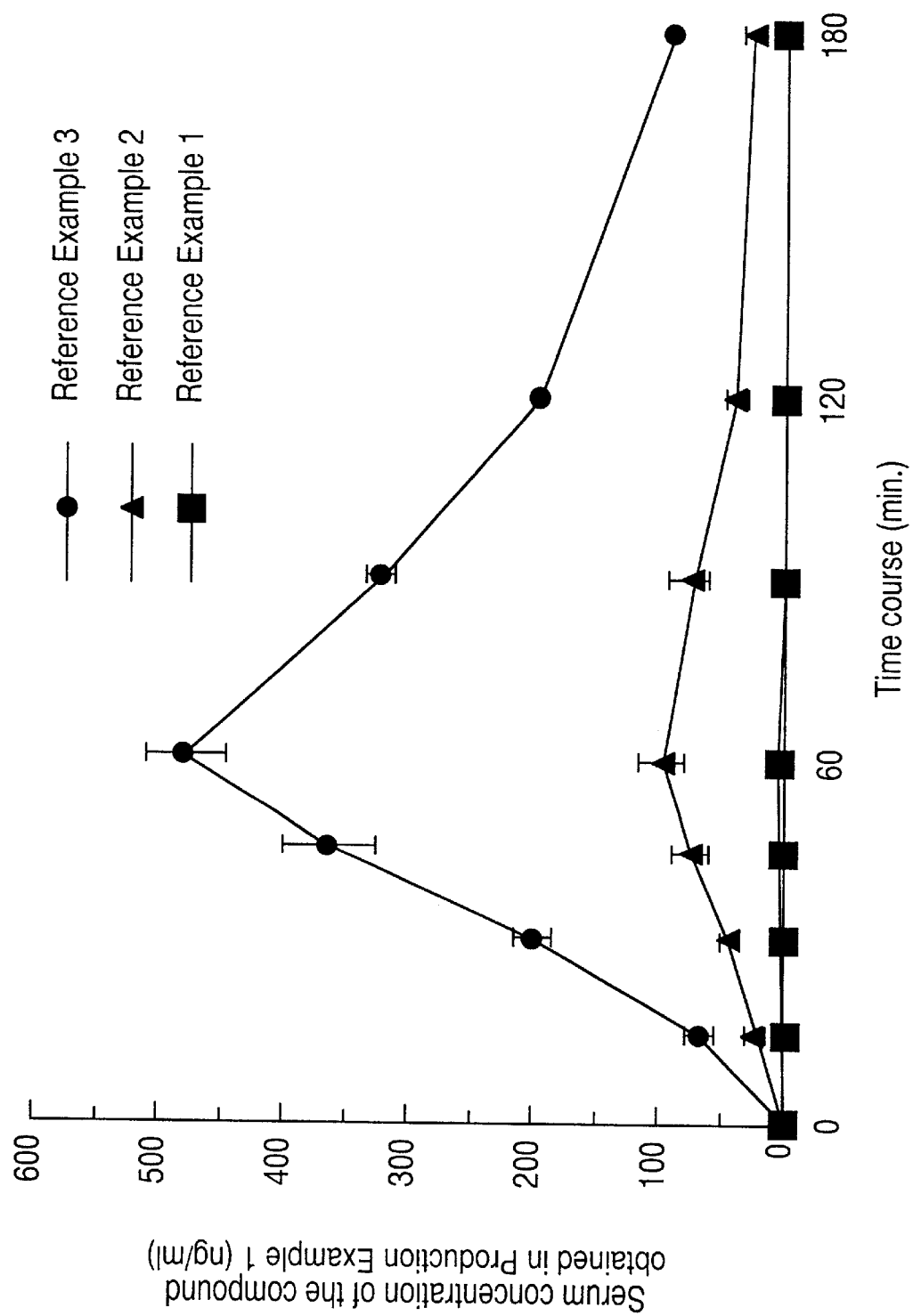

One of example status of electric current application in the present invention is shown as FIGS. 1-1 to 1-3.

In the present invention, as a pretreatment of the first series of electric current application, current application steps, the current density is lower than the one of the initial current application, can be set before the initial current application. In order to obtain desired electric current density of each a step of the first series or of each an electric current application of the further series, it is applicable that the desired current density can be applied from the beginning or that a current density is gradually or progressively elevated to the desired level. In case that the current density is gradually or progressively elevated, it is preferable that the current density is elevated for a short time.

The device which is used for transdermal administration of a GP IIb/IIIa antagonist by iontophoresis according to the present invention is not particularly restricted but includes the device described in JP-A-103494/1997 and the device described in JP-A-56827/1997. For example, the device illustrated in FIG. 2, comprising an anode patch comprising a silver foil electrode 1, a conductive layer 2 containing a hydrophilic gel such as agar, and an electrolyte, a cup-shaped support 3 holding 1 and 2, an adhesive member 4 for affixing the device in position on the skin surface and a porous membrane (drug-holding membrane) for holding a GP IIb/IIIa antagonist in dry condition and a cathode patch comprising a silver chloride foil electrode and an hydrophilic gel such as agar can be used. Preferably, the porous membrane can be separated from the conductive layer before administration, the porous membrane can be affixed to the conductive layer upon administration. As an alternative, in lieu of supporting a GP IIb/IIIa antagonist in said porous membrane, a patch comprising the antagonist dissolved or dispersed in the hydrophilic gel of the conductive layer can be employed. Although the above-mentioned porous membrane can be omitted when GP IIb/IIIa antagonists are employed in the conductive layer, the porous membrane is preferably used in order to support the conductive layer.

Any gel can be used for the above-mentioned hydrophilic gel, as long as it does not adversely affect the skin (irritation, corrosion etc.) and has suitable properies such as good skin contact property (e.g. adhesiveness) and electroconductive property. Typical examples are agar, agarose, etc. Preferable examples of the hydrophilic gels include hydrophilic resins, polymers and mixture thereof. Hydrophilic resins include acrylic resins (e.g. polyacrylamide, polyacrylic acid, alkali metal salts thereof and esters thereof and so on), vinyl resins (e.g. polyvinylpyrrolidone, polyvinyl alcohol, polyvinyl ethyl ether and copolymers thereof and so on), and natural polysaccharides (e.g. tragacanth gum and karaya gum and so on). Polymers include methyl cellulose, hydroxypropyl cellulose, hydroxypropylmethyl cellulose, hyaluronic acid and alkali metal salts thereof, agarose, curdlan and so on. The hydrophilic gel is preferably agar, polyvinyl alcohol, agarose, curdran and so on.

To the hydrophilic gel can be added additives such as preservatives, antioxidants, plasticizers, osmolarity enhancers, dissolution aids, drug absorption promoters, enzyme inhibitors, substances to control drug release, humectants, thickeners, pH regulators and mixtures thereof, etc.

Preservatives include benzalkonium chloride, cetrimide (cetyltrimethylammonium bromide), benzoic acid, benzyl alcohol, Paraben (trade name for methyl-, ethyl-, propyl- and butyl-esters of p-hydroxybenzoic acid), chlorhexidine, chlorobutanol, phenylmercury acetate, phenylmercury borate, phenylmercury nitrate, potassium sorbate, sodium benzoate, sorbic acid, thiomersal (mercurithiosalicylate) and mixtures thereof, etc.

Antioxidants include sodium metabisulfite, butylated hydroxyanisole, butylated hydroxytoluene, vitamins C and E and mixtures thereof, etc.

Plasticizers include diethyl phthalate, dibutyl phthalate, tributyl citrate and mixtures thereof, etc.

Osmolarity enhancers include dimethyl sulfoxide, N,N-dimethylacetamide, N,N-dimethylformamide, 2-pyrrolidone, N-methyl-2-pyrrolidone, 1-dodecylazacycloheptan-2-one and mixtures thereof, etc.

Dissolution aids include cyclodextrins and a mixture thereof such as α-CD, βCD, γCD, and so on.

Drug absorption promoters include fatty acids, fatty acid derivatves, surfactants, alcohols, polyprenyl azacycloalkans and mixtures thereof, etc. The above described fatty acids include oleic acid, lauric acid, myristic acid, palmitic acid, stearic acid, etc. The above described fatty acid derivatives include fatty acid esters, polyalcohol fatty acid esters, polyglyceryl fatty acid esters, fatty acid amides, etc. The above described fatty acid esters include isopropyl myristate, diester sebacate, isopropyl palmitate, ethyl oleate, ethyl laurate, etc. The above described polyalcohol fatty acid esters include glyceryl monooleate, glyceryl monolaurate, glyceryl monostearate, glyceryl dioleate, glyceryl distearate, propylene glycol monocaprylate, diethylene glycol monostearate, propylene glycol monostearate, caprylic/capric triglyceride, etc. The above described polyglyceryl fatty acid esters include tetraglyceryl fatty acid esters (e.g. tetraglyceryl oleate, tetraglyceryl stearate, etc), hexaglyceryl fatty acid esters (e.g. hexaglyceryl oleate, hexaglyceryl laurate, hexaglyceryl stearate, etc), decaglyceryl fatty acid esters (e.g. decaglyceryl oleate, decaglyceryl laurate, decaglyceryl myristate, decaglyceryl stearate, etc), etc. The above described fatty acid amids include lauric acid diethanolamide, stearic acid diethylamino ethylamide, stearic acid dimethylamino propylamide, etc. The above described surfactants include sodium lauryl sulfate, sorbitan monopalmitate, sorbitan monooleate, sorbitan monolaurate, polyoxyethylene sorbitan monooleate (6), polyoxyethylene sorbitan monooleate (20), polyoxyethylene hydrogenated castor oils, block copolymer-non-ionic surfactans (e.g. Pluronics, etc), etc. The above described alcohols include ethyl alcohol, cetyl alcohol, stearyl alcohol, lauryl alcohol, oleyl alcohol, L-menthol, DL-menthol, etc. The above described polyprenyl azacycloalkans include 1-dodecyl azacycloheptan-2-one. Drug absorption promoters also include limonen.

Enzyme inhibitors include aprotinin, camostat mesilate, chymostatin and mixtures thereof, etc.

Substances to control drug release include methyl cellulose, ethyl cellulose, hydroxypropylmethyl cellulose, hydroxypropylmethyl cellulose phthalate, hydroxypropylmethyl cellulose acetate succinate, carboxymethyl cellulose sodium, carboxymethylethyl cellulose, cellulose acetate phthalate, hydroxyethyl cellulose, α-starch, aminoacrylmethacrylate copolymers (Eudragit E, Eudragit RS), methacrylic acid copolymers (Eudragit L, Eudragit S), alginic acid propylene glycol ester (Kimiloid), purified shellac, white shellac, polyethylene glycols of various molecular weights (e.g., PEG-6000, etc.), polyvinyl alcohol, polyvinylpyrrolidone, carboxyvinyl polymer, albumin, collagen, various amino acids, sucrose, glucose and mixtures thereof, etc.

The humectant includes, for instance, (1) polyhydric alcohols, (2) sugar alcohols, (3) amino acids, (4) acidic mucopolysaccharides and so on. Also, humectant includes urea, lecithin, ceramide, liposomes as prepared from synthetic lipid or the like, and so on. These humectants may be used singly or in combination.

Polyhydric alcohols (1) include glycerin, ethylene glycol, propylene glycol, 1,3-butylene glycol, pentaerythritol, polyethylene glycol, adducts in which ethylene oxide is added with these polyhydric alcohols (e.g. dioxyethylene glycol, trioxyethylene glycol, polyoxyethylene glycol, an ethylene oxide-propylene oxide copolymer, a glycerin-ethylene oxide adduct, a penta-erythritol-ethylene oxide adduct, etc.) and so on. Such polyhydric alcohols can be employed independently or in combination. Preferred examples of the polyhydric alcohols include polyhydric alcohols each having 2 to 4 hydroxyl group per molecule, in particular glycerin.

Sugar alcohols (2), include pentitols such as xylitol, sorbitol, mannitol, hexitol such as galactitol and so on. These sugar alcohols may also be used singly or in combination.

Amino acids (3) include (i) an amino acid constituting a protein, (ii) a naturally-occurring amino acid derived or obtained as a metabolite of a microorganism, or an animal or plant component, and (iii) an amino acid obtained by organic synthesis and so on.

(i) The amino acid constituting a protein includes aliphatic monoaminomonocarboxylic acid such as glycine, alanine, valine, leucine, isoleucine and so on; aliphatic hydroxyamino acid such as serine, threonine and so on; acidic amino acid such as aspartic acid, glutamic acid and so on; acidic amino acid amide such as asparagine, glutamine and so on; aromatic amino acid such as phenylalanine, tyrosine, tryptophane and so on; amino acid having pyrrolidine ring such as proline, hydroxyproline and so on; amino acid having pyrrolidone ring such as pyroglutamic acid (pyrrolidone-carboxylic acid) and so on; sulfur-containing amino acid such as methionine, cystine, cysteine and so on, etc. Such amino acid may be employed independently or in combination.

(ii) The naturally-occurring amino acid derived or obtained as a metabolite of a microorganism or an animal or plant component includes aliphatic monoaminomonocarboxylic acid such as L-(α)-aminobutyric acid, L- (γ)-aminobutyric acid, (β)-amino-isobutyric acid, (β)-alanine, homoserine, (α)-methyl-D-serine, O-carbamyl-D-serine, (δ)-hydroxy-(γ)-oxo-norvaline and so on; monoaminodicarboxylic acid such as L-(α)-aminoadipic acid, L-(β)-aminoadipic acid, L-theanine, L-(γ) -methylene-glutamic acid, L- (γ)-methylglutamic acid and so on; diaminomonocarboxylic acid such as L-ornithine, (β)-lysine, (α),(β)-diaminopropionic acid, L-(α), (γ)-diaminobutyric acid and so on; diaminodicarboxylic acid such as diaminopimeric acid and so on; sulfonic acid-containing monoaminomonocarboxylic acid such as cysteic acid and so on; sulfonic acid-containing amino acid such as urine and so on; aromatic amino acids such as kynurenine, 3,4-dioxyphenyl-L-alanine and so on; heterocyclic amino acid such as 2,3-dicarboxyaziridine, (S)-2-amino-3-(isoxazolin-5-on-4-yl)-propionic acid, anticapsin and so on; sulfur-containing amino acid such as lanthionine, S-methyl-L-cysteine and so on; cyclic amino acid such as pipecolic acid, azetidine-2-carboxylic acid, (1R,2S)-2-amino-cyclopentan-1-carboxylic acid and so on; specific functional group-substituted amino acid such as citrulline, alanosine, azaserine and so on, etc.

(iii) The amino acid obtained by organic synthesis includes aliphatic aminocarboxylic acid such as trimethylglycine, 6-aminohexanoic acid, 8-aminooctanoic acid, 12-aminododecanoic acid and so on; aromatic aminocarboxylic acid such as 4-aminobenzoic acid, 4-(aminomethyl)benzoic acid, 4-(N-(carboxymethyl)aminomethyl) benzoic acid and so on, etc.

The amino acid may be used in the form of a salt. The salt of the amino acid includes, for example, a salt with a base (e.g. ammonia, alkali metals (e.g. sodium, potassium) and other inorganic bases, and trimethylamine, triethylamine and other organic bases), and a salt with an acid (hydrochloric acid, sulfuric acid, nitric acid, phosphoric acid and other inorganic acids, and acetic acid, propionic acid, p-toluenesulfonic acid and other organic acids).

Preferred amino acids include an amino acid having a nitrogen-containing heterocycle (e.g. an amino acid having pyrrolidine ring such as proline, hydroxyproline and so on; an amino acid constituting a protein pyrrolidonecarboxylic acid, histidine, tryptophane and so on) or salt thereof. Among them, more preferred amino acids include an amino acid having nonaromatic nitrogen-containing 5-membered heterocycle (e.g. an amino acid having pyrrolidine ring such as proline and hydroxyproline and pyrrolidone-carboxylic acid, and so on) or salt thereof.

(4) The acidic mucopolysaccharides include hyaluronic acid, chondroitin sulfate, and salt thereof (e.g. salt with alkali metals (e.g. sodium, potassium)), etc.

Among these humectants, polyhydric alcohols (in particular glycerin) and amino acids or salts thereof (in particular, an amino acid having a nitrogen-containing heterocycle such as proline, etc.) may preferably be used. The use of the amino acids (in particular, proline and an amino acid having a nitrogen-containing heterocycle such as proline, etc.) or its salt ensures remarkable mitigation of skin irritation accompanied with an electric current application, and provides an increased quantity of applied electricity in an application of an electric current application succeeding to the initial current application step in a case that transdermal absorption is conducted in plural times at periodic intervals, and hence ensures an improved transdermal absorptivity.

Thickeners include, for example, locust bean gum, xanthan gum and so on. These thickeners may also be used singly or in combination.

When GP IIb/IIIa antagonist is a salt with hydrochloric acid and the antagonist is added to the hydrophilic gel, pH regulators can be added to the hydrophilic gel in order to prevent pH-dropping by addition of the antagonist. The pH regulators include a basic amino acid such as lysine, arginine, histidine L-4-oxalysine, L-4-oxolysine, (3R,5R)-3,6-diamino-5-hydroxyhexanoic acid; a base consisting of nucleic acids (e.g. purine, pyrimidine, guanin, etc.); an amine having not less than 100 of molecular weight (e.g. monoethanolamine, diethanolamine, triethanolamine, methylglucamine, caffeine, cholestyramine hydride (cholestyramine-OH) produced by substituting hydroxide ion for chloride ion in addition to cholestyramine) and so on.

The above-mentioned electrolytes include benzoic acid, citric acid and salt thereof (e.g. salt with sodium, etc.) and so on.

The above-mentioned porous membranes include membrane having a high wettability with respect to water, such as hydrophilized hydrophobic (or water-repellent) polymer membrane, hydrophobic polymer membrane containing a hydrophilic substance, and so on.

As the hydrophilized hydrophobic polymer membrane, there may be mentioned, for example, membranes formed with a hydrophilized fluororesin (e.g. a membrane of a homo- or co-polymer which comprises, as a constitutive component, a fluorine-containing monomer introduced with a hydrophilic group such as "Hydrophilic Durapore" manufactured by Nippon Millipore Co., Ltd., and a surface-modified membrane, in which the surface of a homo- or co-polymer comprising a fluorine-containing monomer as constitutive component is modified to be hydrophilic, such as "Hydrophilized Polytetrafluoroethylene", Toyo Roshi Co., Ltd.), membranes formed with a hydrophilized polysulfone (e.g."SUPOR", Gelman Science Co., Ltd.), membranes made from a hydrophilized cellulose derivatives (e.g. hydrophilized cellulose mono-acetate or hydrophilized cellulose tri-acetate) or the like (e.g. various filter papers and ion exchange filter papers manufactured by Toyo Roshi Co., Ltd.) and so on. The fluorine-containing monomer introduced with a hydrophilic group includes, for instance, a fluoroethylene (1-fluoroethylene) introduced with a hydrophilic group, a vinylidene fluoride (i.e. vinylidene fluoride as 1,1-difluoroethylene) and 1,2-difluoroethylene, each of which is introduced with a hydrophilic group. As examples of the polymer formed with such monomer, there may be mentioned a hydrophilized polyfluoroethylene, a hydrophilized fluoroethylene-tetrafluoroethylene copolymer, a hydrophilized fluoro-ethylene-hexafluoropropylene copolymer, a hydrophilized ethylene-fluoroethylene copolymer, a hydrophilized ethylene-chlorotrifluoroethylene copolymer, a hydrophilized poly (vinylidene fluoride), a hydrophilized fluoroethylene-vinylidene fluoride copolymer, a hydrophilized ethylene-vinylidene fluoride copolymer and so forth. The species of the hydrophilic group introduced into the fluorine-containing monomer is not strictly limited, and includes, for example, a hydroxyl group, a carboxyl group, an amino group, an N-substituted amino group (e.g. a mono- or di-$C_{1-4}$ alkylamino group), a (poly)oxyalkylene group and other ether groups, a hydrophilic alkyl group (e.g. hydroxymethyl, hydroxyethyl, hydroxypropyl and other hydroxy-$C_{1-4}$ alkyl groups, a carboxymethyl group, a carboxyethyl group and other carboxy-$C_{1-4}$ alkyl groups, aminomethyl, aminoethyl and other amino-$C_{1-4}$ alkyl groups, methylaminomethyl, dimethylaminomethyl, dimethylaminoethyl and other mono- or di-$C_{1-4}$ alkylamino-$C_{1-4}$ alkyl groups, etc.). These hydrophilic groups may practically be bonded to a carbon atom as a substitute for a hydrogen atom.

The hydrophilized fluororesin may practically comprise a repeating unit shown by the following formula.

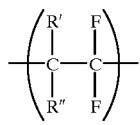

wherein R' and R" respectively represent a hydrophilic alkyl group.

As the hydrophilic alkyl group, there may be mentioned, for instance, a hydroxyalkyl group (in particular, a hydroxy-$C_{2-3}$ alkyl group) and a (poly)oxyalkylene group (especially, a (poly)oxy-$C_{2-4}$ alkylene group). The hydroxyalkyl group may be derived from a polymerizable compound having a hydroxyl group (e.g. hydroxyethyl (meth)acrylate, hydroxypropyl (meth)acrylate or 4-hydroxybutyl (meth)acrylate). The (poly)oxyalkylene group may be derived from a polymerizable compound having an ether group, such as a (poly)oxyalkylene glycol mono(meth)acrylate (e.g. diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, tripropylene glycol mono(meth) acrylate, tetrapropylene glycol mono(meth)acrylate, polypropylene glycol mono(meth)acrylate, etc.), a (poly) oxyalkylene glycol di(meth)acrylate (e.g. ethylene glycol di(meth)acrylate, diethylene glycol di(meth)acrylate, triethylene glycol di(meth)acrylate, tetraethylene glycol di(meth) acrylate, polyethylene glycol di(meth)acrylate, propylene glycol di(meth)acrylate, dipropylene glycol di(meth) acrylate, tripropylene glycol di(meth)acrylate, tetrapropylene glycol di(meth)acrylate, polypropylene glycol di(meth) acrylate, tetramethylene glycol di(meth)acrylate and so forth). Such hydrophilic alkyl group may be introduced by means of graft polymerization of the polymerizable compound to the surface, including pores, of a porous fluororesin membrane, or introduced by coating with the polymer derived from the polymerizable compound.

The hydrophilized hydrophobic membrane is prepared by physically treating hydrophobic polymer membrane with a hydrophilic substance. Examples of such hydrophilized hydrophobic membranes include various membranes prepared from hydrophobic polymer membrane incorporated with a suitable wetting agent (e.g. glycerin, polyvinylpyrrolidone, etc.), such as a hydrophilized cellulose acetate membrane (e.g. "Asymmetric Ultrafilter" manufactured by Sartorius Co., Ltd.; "Cellulose Acetate Type Membrane" manufactured by Toyo Roshi Co., Ltd.), a hydrophilized polycarbonate membrane (e.g. "Isopore Membrane" manufactured by Millipore Co., Ltd.), a hydrophilized polytetrafluoroethylene membrane (e.g. "Omnipore Membrane" manufactured by Millipore Co., Ltd.) and a hydrophilized polysulfone membrane (e.g. "HT Tuffryn" manufactured by Gelman Science Co., Ltd.), a hydrophilized non-woven membrane such as a polyester non-woven treated with cellulose acetate and wetting agents (e.g. "Coated Type Membrane" manufactured by Toyo Roshi Co., Ltd.).

These porous membranes have an extremely low adsorptivity for a physiologically active peptide or protein and provide a high permeability of a drug-containing solution or a dissolution liquid for dissolving the drug and high dissolution rate of the drug. The preferred membrane includes a membrane having a low adsorptivity for a protein and a high retentivity for the drug, such as a hydrophilized fluororesin membrane and a hydrophilized cellulose derivative membrane. Such cellulose derivative is exemplified by cellulose acetate, methylcellulose, ethylcellulose, hydroxypropylcellulose, hydroxypropylmethylcellulose phthalate, etc. Among them, a hydrophilized poly (vinylidene fluoride) (e.g. "Hydrophilic Durapore" manufactured by Millipore Co., Ltd.) and a hydrophilized cellulose acetate membrane (e.g. "Cellulose Acetate Type Membrane" manufactured by Toyo Roshi Co., Ltd.), and a hydrophilized polyester non-woven coated with cellulose acetate and wetting agents (e.g. "Coated Type Membrane" manufactured by Toyo Roshi Co., Ltd.) can advantageously be employed.

The pore size of the porous membrane can be selected within a range not interfering with retention amount (holding amount) and/or releasability of the drug and ensuring rapid release of the drug after the contact with a dissolution liquid, and providing formation of a highly concentrated drug dissolution layer on a surface or side to be made contact with a skin, and the mean pore size is about 0.01 to 20 μm, preferably about 0.1 to 15 μm (e.g. about 0.1 to 10 μm) and more preferably about 1 to 10 μm (e.g. about 2 to 8 μm), for example. The porosity (percentage of void) of the porous membrane may be for instance about 60 to 90%, preferably about 65 to 90% and more preferably about 65 to 85%. The pore of the porous membrane may be formed by a conventional technologies such as extending process which comprises extending the film in a film-forming step, fluid-extending, phase-separation, elution or irradiation of a high energy radiation.

The thickness of the porous membrane may be selected within a range according to the holding amount (retention amount) of the drug, and is, for example, about 0.1 to 500 μm, preferably about 1 to 300 μm and more preferably about 10 to 200 μm. The porous membrane may practically have a thickness of about 20 to 150 μm.

The area of the skin-contacting surface of the porous membrane may liberally be selected, and is for instance about 0.5 to 100 cm$^2$, preferably about 1 to 50 cm$^2$, more preferably about 2 to 25 cm$^2$ (e.g. about 2 to 20 cm$^2$). The porous membrane may be non-deformable, but it may preferably have flexibility or softness.

The above-mentioned porous membrane may be treated with an ionic surfactant for the purpose of further inhibiting adsorption of a protein. The ionic surfactant (surface active agent) includes anionic surfactants, cationic surfactants and amphoteric surfactants. As examples of the anionic surfactant, there may be mentioned metallic soaps of fatty acids, alkyl sulfates (e.g. a sodium salt, etc.), alkylbenzenesulfonates (e.g. a sodium salt, etc.), alkylnaphthalenesulfonates, (α)-olefin sulfonates (e.g. a sodium salt), N-acylamino acid salts (e.g. a sodium salt, etc.) and dialkyl-2-sulfosuccinates (e.g. a sodium salt, etc.). These anionic surfactants may be used singly or in combination.

The cationic surfactant includes, for instance, N-ethylalkaneamideammonium halides (e.g. N-ethyl-$C_{8-20}$ alkaneamideammonium chloride, etc.), alkylpyridinium halides (e.g. an N-$C_{10-20}$ alkylpyridinium bromide, etc.), quaternary ammonium salts and so forth. Examples of the quaternary ammonium salt include alkyltrimethylammonium halides (e.g. a $C_{8-20}$ alkyl-trimethylammonium chloride, etc.), dialkyldimethylammonium halides (e.g. a di-$C_{8-20}$ alkyl-dimethylammonium chloride, etc.), alkylbenzyl-dimethylammonium halides shown by the following formula:

$$[C_6H_5CH_2N(CH_3)_2R]^+X^-$$

wherein R represents an alkyl group and X represents a halogen atom, (e.g. a $C_{8-20}$ alkylbenzyldimethylammonium chloride (benzalkonium chloride), a 4-$C_{1-10}$ alkyl-phenyloxyethoxyethylbenzyldimethylammonium chloride (e.g. benzethonium chloride)) and so forth. Such cationic surfactants can also be employed independently or in combination. Examples of the amphoteric surfactant include an alkyl betaine, an alkyl diethylenetriaminoacetate and the like.

Preferable ionic surfactant includes cationic surfactants, in particular quaternary ammonium salts. The alkylbenzyldimethylammonium halides shown by the above-mentioned formula (e.g. benzalkonium chloride, benzethonium chloride) can advantageously be employed among others.

The treating amount of the ionic surfactant relative to the porous membrane is for example about 0.10 to 50 μg, preferably about 0.10 to 30 μg and more preferably about 0.12 to 12 μg of the ionic surfactant relative to 1 cm² of the porous membrane. The treating amount of the ionic surfactant may be about 0.001 to 10% by weight, preferably about 0.005 to 5% by weight and more preferably about 0.01 to 1% by weight relative to the porous membrane. The porous membrane may practically be treated with about 0.005 to 1% by weight, relative to the porous membrane, of the ionic surfactant.

In the above-mentioned anode-patch, for example, a foil silver/silver chloride electrode, a print silver electrode, a print silver/silver chloride electrode or the like can be used for an anode electrode instead of a foil silver electrode. The foil silver electrode means an electrode made by silver foil. The foil silver/silver chloride electrode is a foil silver electrode of which the surface is partially oxidized by chemical methods to convert it to silver chloride. The print silver electrode is one where silver is printed on surface of a sheet. The print silver/silver chloride electrode is one where a mixture of silver and silver chloride is printed on surface of a sheet.

In the above-mentioned cathode-patch, for example, a foil silver/silver chloride electrode, a print silver/silver chloride electrode or the like can be used for a cathode electrode instead of a foil silver chloride electrode.

The ratio of silver to silver chloride in the foil silver/silver chloride electrode or the print silver/silver chloride electrode used for either the anode or the cathode is about 1/0.1 to 1,000 (weight ratio) of silver/silver chloride.

The print silver/silver chloride electrode is preferably selected for either the anode or the cathode since it can be obtained cost-effectively. It is more preferable to use the print silver/silver chloride electrode for both anode and cathode, to mix a GP IIb/IIIa antagonist with hydrophilic gels of both anode and cathode, and to periodically reverse the polarities of the electrodes, e.g., anode to cathode or cathode to anode. Such electrode-revering over is repeatedly done every about 1 to 60 minutes. The electrode-reversing over itself is done for a very short time which is negligible, so that it is not like the interval before each current application in the further series of electric current application, as mentioned before. The electric current application should be recognized as being carried out continuously while the electrode-revering over is repeatedly done.

GP IIb/IIIa antagonists in the present invention is not particularly restricted, but can be selected from the known GP IIb/IIIa antagonists or salts thereof. The known GP IIb/IIIa antagonists include snake poison (venom) peptides each having antagonistic activity against GPIIb/IIIa, such as barbourin, peptides having Arg-Gly-Asp sequence, such as Arg-Gly-Asp-Ser, Gly-Arg-Gly-Asp-Ser-Pro, SK&F-106760 (cyclo-S,S-(Ac-Cys($N^\alpha$-methyl)Arg-Gly-D-Asn-penicillamine)-$NH_2$, and other peptide-like compounds having a similar function or activity, such as sibrafiban, lefradafiban (S)-4-((4-amidinobenzoyl)glycyl)-3-methoxycarbonylmethyl-2-oxopiperazine-1-acetic acid, (S)-4-(4-guanidinobenzoylamino)acetyl-3-(3-(4-guanidinobenzoylamino))propyl-2-oxopiperazine-1-acetic acid hydrochloride, MK-383 (2-S-(n-butylsulfonylamino)-3-(4-(N-piperidin-4-yl)butyloxyphenyl))-propionic acid hydrochloride, L-700462 (L-Tyr-N-(butylsulfonyl)-O-(4-(piperidinyl)butyl) mono-hydrochloride), SC-56484 (ethyl ((4-(aminoiminomethyl)phenyl)amino)-1,4-dioxybutyl) amino-4-pentinoate), lamifiban (Ro-44-9883) ((1-(N-(p-amidinophenyl)-L-Tyr)-4-piperidinyl)acetic acid), DMP728 (cyclic(D-2-aminobutylyl-N-2-methyl-L-Arg-Gly-L-Asp-3-aminomethyl-benzoic acid) methanesulfonate, compounds described in WO 97/49382, such as {4-[6-(2-piperidine-4-yl-(E)-vinyl)-1H-indazol-3-yl]-piperadine-1-yl}-acetic acid, compounds described in WO 97/49385, such as $N^3$-[2-{3-(4-formamidinophenyl)-isoxazolin-5-(R)-yl}-acetyl-$N^2$-(n-butyloxycarbonyl)-2,3-(S)-diaminopropanoic acid or methyl-N3-[2-{3-(4-formamidinophenyl)-isoxazolin-5-(R)-yl}-acetyl-N2-(n-butyloxycarbonyl)-2,3-(S)-diaminopropionate methanesulfonate salt, intrifiban

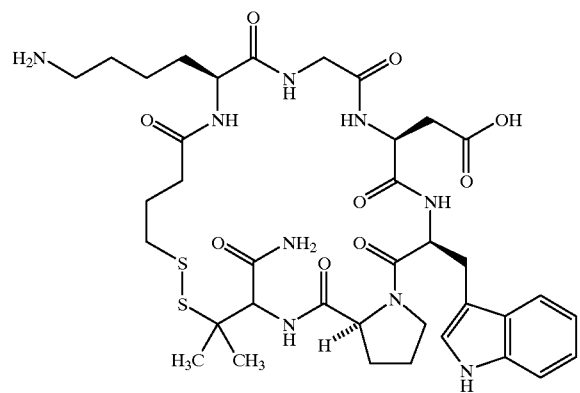
tirofiban

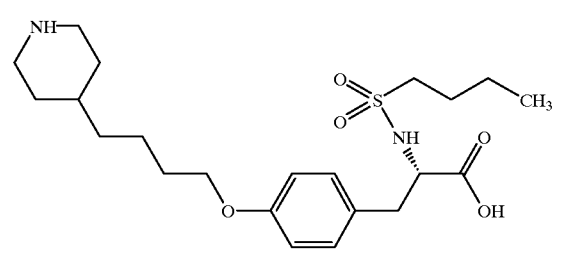
fradafiban

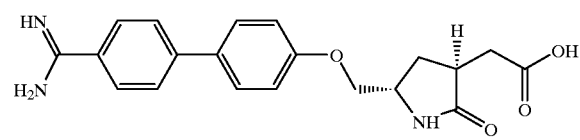

a compound of the formula

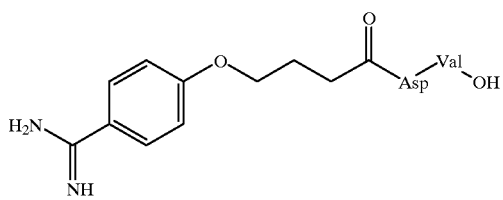

a compound of the formula

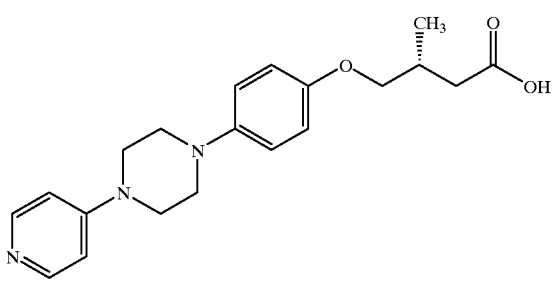

a compound of the formula

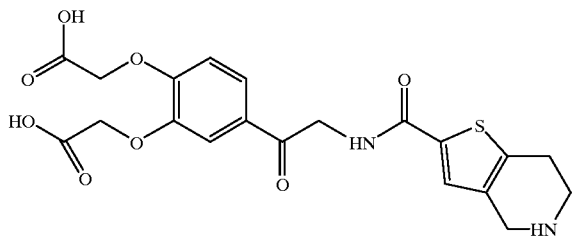

pentamidine xemilofiban

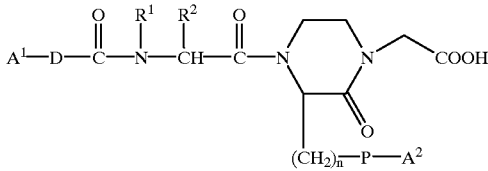

orbofiban

, ETC.

Preferably, the GP IIb/IIIa antagonist in the present invention is a water-soluble compound.

Further, those compounds which contain both "proton-releasing groups (groups capable of releasing a proton)" and "proton-accepting groups" and in which the number of protons which may be accepted by said "proton-accepting groups" outnumber the protons which may be released by said "proton-releasing groups" are preferred. The proton-releasing group means a Brønsted acid group such as a carboxyl group, a phosphoric acid group or a sulfonic acid group, preferably a carboxyl group. The proton-accepting group is a group capable of accepting a proton from a counterpart group, i.e. a Brønsted base, such as a group containing a positively chargeable nitrogen atom. As specific examples of the proton-accepting group, there may be mentioned amino, amidino and guanidino, each of which may optionally be substituted. Preferred proton-accepting groups are unsubstituted amino, unsubstituted amidino, unsubstituted guanidino, and $C_{1-4}$ alkyl-substituted secondary or tertiary amino (particularly ethylamino), amidino and guanidino.

Preferred GP IIb/IIIa antagonists in the present invention are compounds having a 2-piperazinone-1-acetic acid skeleton. More preferred are compounds (I) of the formula:

$$A^1-D-\overset{O}{\underset{}{C}}-\overset{R^1}{\underset{}{N}}-\overset{R^2}{\underset{}{CH}}-\overset{O}{\underset{}{C}}-N\underset{(CH_2)_n-P-A^2}{\overset{O}{\underset{}{\bigcirc}}}N-COOH \quad (I)$$

[wherein the symbols are respectively as defined with respect to the formula (I) given previously], and salts thereof.

In the above formula (I), $A^1$ and $A^2$ independently are a proton-accepting group.

In the above formula (I), the proton-accepting group means a group which accepts a proton from a relevant group, namely a Brønsted base as exemplified by a group containing nitrogen atom capable of being positively charged. Specific examples of the proton-accepting group include optionally substituted amino, amidino and guanidino groups. Preferable examples of the proton-accepting group include unsubstituted amino, amidino and guanidino groups, or secondary or tertiary amino groups (especially ethylamino), amidino or guanidino groups substituted with a $C_{1-4}$ alkyl group.

Examples of the substituents of optionally substituted amino, amidino and guanidino groups include chain-like or cyclic hydrocarbon groups such as $C_{1-6}$ alkyl groups (e.g. methyl, ethyl, propyl, isopropyl, butyl, sec-butyl, tert-butyl, pentyl and hexyl), $C_{2-6}$ alkenyl groups (e.g. vinyl, allyl, isopropenyl, butenyl, isobutenyl and sec-butenyl), $C_{2-6}$ alkynyl groups (e.g. propargyl, ethynyl, butynyl and 1-hexyl), $C_{3-6}$ cycloalkyl groups (e.g. cyclopropyl, cyclobutyl, cyclopentyl and cyclohexyl), $C_{6-14}$ aryl groups (e.g. phenyl, tolyl, xylyl, 1-naphthyl, 2-naphthyl, biphenyl, 2-indenyl and 2-anthryl, especially phenyl group), and $C_{7-16}$ aralkyl groups (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl, especially benzyl group); $C_{1-4}$ alkyl groups (e.g. methyl) substituted with carbamoyloxy optionally substituted with $C_{1-4}$ alkyl (e.g. N,N-dimethylaminocarbonyloxy), $C_{2-5}$ alkanoyloxy (e.g. pivaloyloxy) or a 5- or 6-membered heterocyclic group (e.g. a 5-membered cyclic group containing, besides carbon atoms, 1 to 4 hetero-atoms selected from oxygen atom, sulfur atom and nitrogen atom, such as 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4-or 5-pyrazolyl, 2-, 4- or 5-imidazolyl, 1,2,3-triazolyl, 1,2,4-triazolyl and 1H- or 2H-tetrazolyl, a 6-membered cyclic group, preferably pyrrolidin-1-yl and morpholino, containing, besides carbon atoms, 1 to 4 hetero-atoms selected from oxygen atom, sulfur atom and nitrogen atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiadinyl, 1,3-thiadinyl, piperazinyl, triazinyl, 3- or 4-pyridazinyl, pyrazinyl, N-oxido-3- or 4-pyridazinyl); $C_{2-8}$ alkoxycarbonyl (e.g. methoxycarbonyl, ethoxycarbonyl, propoxycarbonyl, butoxycarbonyl, pentyloxycarbonyl, n-hexyloxycarbonyl and n-octyloxycarbonyl); $C_{1-8}$ alkylaminocarbonyl (e.g. n-hexylaminocarbonyl and n-octylaminocarbonyl); $C_{2-8}$ alkoxycarbonyloxy (e.g. methoxycarbonyloxy, ethoxycarbonyloxy, propoxycarbonyloxy, butoxycarbonyloxy, pentyloxyoxycarbonyloxy, n-hexyloxycarbonyloxy and n-octyloxycarbonyloxy, preferably methoxycarbonyloxy); and 5- or 6-membered heterocyclic groups (e.g. a 5-membered cyclic group containing, besides carbon atoms, 1 to 4 hetero-atoms selected from oxygen atom, sulfur atom and nitrogen atom, such as 2- or 3-thienyl, 2- or 3-furyl, 1, -2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl and 1H- or 2H-tetrazolyl, a 6-membered cyclic group, preferably e.g. tetrahydrofuran-2-yl, containing, besides carbon atoms, 1 to 4 hetero-atoms selected from oxygen atom, sulfur atom and nitrogen atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiadinyl, 1,3-thiadinyl, piperazinyl, triazinyl, 3- or 4-pyridazinyl, pyrazinyl, N-oxido-3- or 4-pyridazinyl). And, in the case where two or more substituents of the amino, amidino or guanidino group exist, they may be combined to form a 5- or 6-membered heterocyclic group (e.g. pyrrolidine, piperidine, morpholine or imidazoline).

Preferable example of $A^1$ and $A^2$ include (1) amidino and guanidino groups which may be substituted with $C_{2-8}$ alkoxycarbonyloxy, and (2) amino groups which may be oxadiazolyl groups which may be substituted with oxo or $C_{1-4}$ alkyl which may be substituted with halogen, and unsubstituted amino, amidino or guanidino groups are more preferable.

In the above formula (I), D is a spacer having a 2- to 6-atom chain optionally bonded through a hetero-atom and/or a 5- or 6-membered ring (provided that the 5- or 6-membered ring is, depending on its bonding position, counted as 2- or 3-atom chain). The spacer of D means a linear interval between $A^1$ and

and means having a interval which is lined with 2 to 6 atoms between them in the present invention.

In the above formula (I), examples of hetero-atoms in the spacer having a 2- to 6-atom chain (2- to 6-membered chain) optionally bonded through a hetero-atom and/or a 5- or 6-membered ring include N, O and S. And, the 5- or 6-membered ring may be carbocyclic one or a heterocyclic one containing 1 to 4 hetero-atoms selected from N, O and S or a saturated ring or an unsaturated ring such as aromatic ring. Examples of such 5- or 6-membered ring include the following;

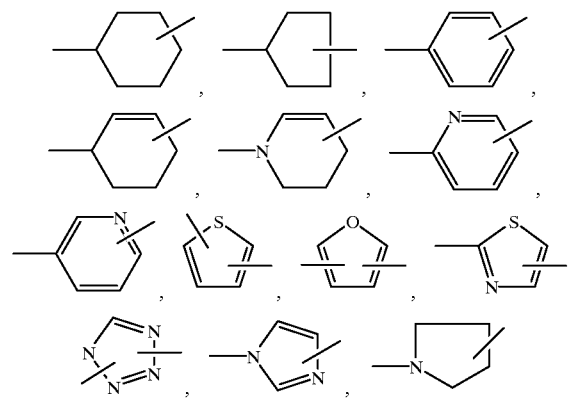

And, the above-mentioned 5- or 6-membered ring is preferably one having no bond at the adjacent position on the ring. The above-mentioned 5- or 6-membered ring is preferably one having a bond at the second or third position to one another on the ring. Usually, even if the ring is saturated or unsaturated, it is regarded as 2- to 3-atom chain (2- to 3-membered chain), and a group having a 2- to 6-atom chain as D itself is preferable. As the hetero-atom existing in the spacer shown by D, nitrogen is preferable above all, and, D bonded to a group shown by $A^1$, such as amidino group existing through —NH— group, is especially preferable. And, the above-mentioned 5- or 6-membered ring may be bonded to the adjacent amidino group directly or to a group shown by $A^1$ such as amidino group through —NH— group, and further to a group shown by $A^1$ such as amidino group through methylene chain.

And, D may be such one as the adjacent carbonyl group bonded directly to the above-mentioned 5- or 6-membered ring, or bonded through methylene chain or bonded through a hetero atom. The methylene chain in D may be substituted with a group of the formula

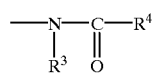

wherein R³ is a hydrogen atom or a lower (C₁₋₄) alkyl group optionally substituted with an optionally substituted phenyl group; and R⁴ is a lower (C₁₋₄) alkyl group optionally substituted with an optionally substituted phenyl group, an optionally substituted phenyl group or benzyloxy group.

Examples of substituents of the optionally substituted phenyl group as the substituent to the lower (C₁₋₄) alkyl group of R³ or R⁴ include lower (C₁₋₄) alkyl (e.g. methyl, ethyl), lower (C₁₋₄) alkoxy (e.g. methoxy, ethoxy), halogen (e.g. fluoro, chloro, bromo), and hydroxyl group.

Example of the lower (C₁₋₄) alkyl group of R³ or R⁴ include methyl and ethyl.

Preferable typical groups shown by D include those of the formula

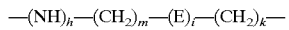

wherein h and i each is 0 or 1; m and k each is 0, 1 or 2; and E is the above-mentioned 5- or 6-membered ring, especially cyclohexane ring, benzene ring, piperidine or a group of the formula

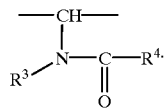

As E, a 5- or 6-membered ring is especially preferable. And, as h, 0 or 1, as m, 0, 1 or 2, and as k, 0are respectively preferable. Among 5- or 6-membered rings shown by E, benzene ring and cyclohexane ring are preferable, and benzene ring is especially preferable.

In the above-mentioned the formula (I), for example, A¹-D- can be included the formula

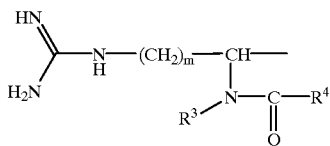

wherein R³, R⁴ and m are of the same meaning as defined above, as groups derived from arginine or homoarginine.

As D, groups of the formula

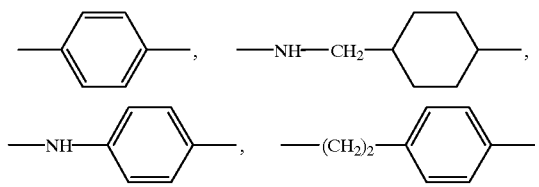

(among others, above all

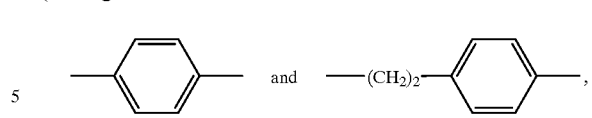

especially

are especially preferable.
(in these groups, either of the bonds may be bonded to A¹)

In the above formula (I), R¹ is a hydrogen atom or a hydrocarbon group.

As the hydrocarbon shown by R¹, mention is made of chain-like or cyclic hydrocarbon groups including C₁₋₆ alkyl groups (e.g. methyl, ethyl, propyl, isopropyl, butyl, sec-butyl, tert-butyl, pentyl and hexyl), C₂₋₆ alkenyl groups (e.g. vinyl, allyl, isopropenyl, butenyl, isobutenyl and sec-butenyl), C₂₋₆ alkynyl groups (e.g. propargyl, ethynyl, butynyl and 1 hexynyl), C₃₋₆ cycloalkyl groups (e.g. cyclopropyl, cyclobutyl, cyclopentyl and cyclohexyl), C₆₋₁₄ aryl groups (e.g. phenyl, tolyl, xylyl, 1-naphthyl, 2-naphthyl, biphenyl, 2-indenyl and 2-anthryl, especially phenyl group), and C₇₋₁₆ aralkyl groups (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl, especially benzyl group), and as R¹, are preferable hydrogen, lower (C₁₋₄) alkyl or benzyl (especially hydrogen).

In the above formula (I), R² is a hydrogen atom or a residual group formed by removing —CH(NH₂)COOH from an a-amino acid.

As the group shown by R², any of the residual groups formed by removing —CH(NH₂)COOH from an α-amino acid can be mentioned. And, R¹ and R² may be combined to form a 5- or 6-membered ring. Preferable examples of such 5- or 6-membered ring include rings as shown below,

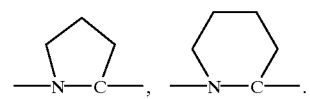

Usually, preferable examples of R² include residual groups of essential amino acids. Especially preferable examples of R² include a hydrogen atom, lower (C₁₋₄) alkyl groups, lower (C₁₋₄) alkyl groups substituted with an optionally substituted phenyl group, lower (C₁₋₄) alkyl groups substituted with hydroxyl group and lower (C₁₋₄) alkyl groups substituted with carbamoyl group. More specifically, hydrogen, methyl, isopropyl, sec-butyl, isobutyl, hydroxylmethyl, benzyl, p-hydroxybenzyl, p-methoxybenzyl, carbamoylmethyl and carbamoylethyl which are mentioned as typical examples.

As substituents optionally substituted on the benzene ring of optionally substituted phenyl group as the substitutent of the lower (C₁₋₄) alkyl of the above R², mention is made of, for example, lower (C₁₋₄) alkyl groups (e.g. methyl, ethyl, propyl, isopropyl, n-butyl and sec-butyl), lower (C₁₋₄) alkoxy groups (e.g. methoxy and ethoxy), halogen (e.g. chlorine, fluorine and bromine) and hydroxyl group, of which the lower (C₁₋₄) alkoxy group is preferable.

As the group or atom shown by $R^2$, hydrogen atom or $C_{1-4}$ alkyl group substituted with phenyl group optionally substituted with $C_{1-4}$ alkoxy are preferable, p-hydroxybenzyl, p-methoxybenzyl or hydrogen atom (more preferably p-methoxybenzyl or hydrogen atoms especially hydrogen atom) are more preferable.

In the above-mentioned formula (I), n is an integer of 0 to 8 (preferably 1 to 4 especially 2 or 3).

In the above formula (I), P is a spacer having a 1- to 10-atom chain optionally bonded through a hetero-atom and/or a 5- or 6-membered ring (provided that the 5- or 6-membered ring is, depending on its bonding position, counted as 2- or 3-atom chain).

In the above formula (I), P is a spacer having a 1- to 10-atom chain optionally bonded through a hetero-atom and/or a 5- or 6-membered ring (provided that the 5- or 6-membered ring is, depending on its bonding position, counted as 2- or 3-atom chain).

The spacer of P means a linear interval between $(CH_2)n$ and $A^2$, and means having a interval which is lined with 1 to 10 atoms between them in the present invention. As the spacer having 1- to 10-atom chains (1- to 10-membered chain) optionally bonded through hetero-atoms and/or a 5- or 6-membered ring, mention is made of a divalent hydrocarbon group optionally bonded through 1 to 4 (preferable 1 or 2) groups selected from

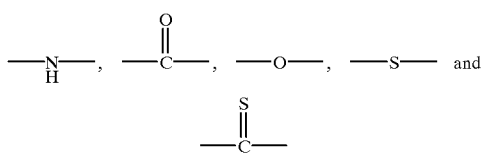

and/or a 5- or 6-membered ring (the 5- or 6-membered ring may be carbocyclic or heterocyclic containing 1 to 4 heteroatoms selected from N, O and S, which may be saturated ring or an unsaturated one such as an aromatic ring; as the carbocyclic one, for example,

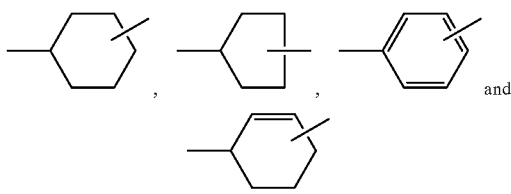

are mentioned, and benzene ring and cyclohexane ring are preferable, and especially benzene ring is preferable; as the heterocyclic ring mentioned are, a 5-membered cyclic group containing, besides carbon atoms, 1 to 4 hetero-atoms selected from, for example, oxygen atom, sulfur atom and nitrogen atom, as exemplified by 2- or 3-thienyl, 2- or 3-furyl, 1-, 2- or 3-pyrrolyl, 1-, 2- or 3-pyrrolidinyl, 2-, 4- or 5-oxazolyl, 2-, 4- or 5-thiazolyl, 3-, 4- or 5-pyrazolyl, 2-, 4- or 5-imidazolyl, 1,2,3-triazolyl, 1,2,4-triazolyl, and 1H- or 2H-tetrazolyl, and, a 6-membered cyclic group containing, besides carbon atoms, 1 to 4 hetero-atoms selected from oxygen atom, sulfur atom and nitrogen atom, as exemplified by 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidinyl, pyranyl, thiopyranyl, 1,4-oxazinyl, 1,4-thiazinyl, 1,3-thiazinyl, piperazinyl, triazinyl, 3- or 4-pyridazinyl, pyrazinyl, and N-oxido-3- or 4-pyridazinyl, and piperazine or piperidine is preferable).

As a more preferable spacer having 1- to 10-atom chains optionally bonded through hetero-atoms and/or a 5- or 6-membered ring, mention is made of a divalent hydrocarbon group optionally bonded through 1 to 4 (preferably 1 or 2) groups selected from

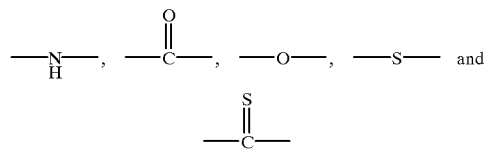

And, in the above-mentioned formula (I), P is a group represented by, for example, the formula,

wherein Z is a one selected from

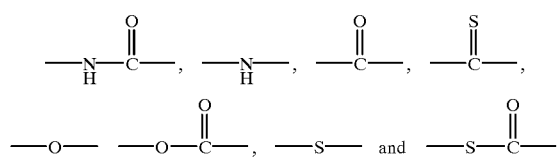

(either bond may be bonded to B) or a bond, and B is a group

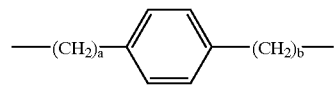

(a and b are an integer of 0 to 2 (preferably 0 or 1), and c is an integer of 1 to 5) or a bond (excluding the case where Z and B are both bonds).

Among the groups shown by the above Z, those represented by

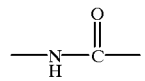

(either of the bonds may be bonded to B) are preferable.

Among the groups shown by the above B, those represented by

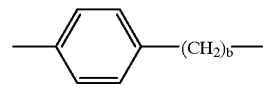

or

wherein b is an integer of 0 to 2 (preferably 0 or 1), and d is an integer of 1 to 4, are preferable. Further preferable groups shown by the above B include

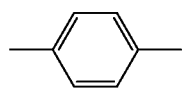

or —$(CH_2)_d$— wherein d is an integer of 1 to 4.

Among the compounds represented by the above-mentioned formula (I) or their salts, the compounds (Ia) of the formula

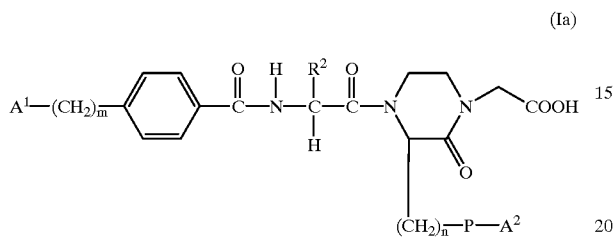

(Ia)

wherein $A^1$ and $A^2$ independently are an optionally substituted amino, amidino or guanidino group, an amidoxime group optionally having a substituent on the oxygen atom, or an optionally substituted oxadiazolyl or thiadiazolyl group, $R^2$ is hydrogen, a lower ($C_{1-4}$) alkyl group, a lower ($C_{1-4}$) alkyl group substituted with an optionally substituted phenyl group, a lower ($C_{1-4}$) alkyl group substituted with hydroxyl group or a lower ($C_{1-4}$) alkyl group substituted with carbamoyl group, P is a divalent hydrocarbon optionally bonded through 1 to 4 groups selected from

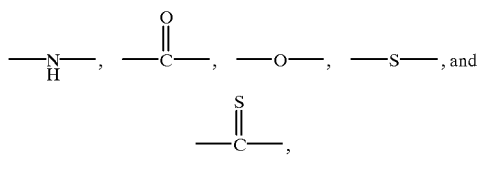

Y is an optionally esterified or amidated carboxyl group, m is an integer of 0 to 2, and n is an integer of 1 to 4, and their salts are preferable.

Further preferable examples of the above-mentioned compounds (Ia) and their salts include compounds (Ia) wherein $A^1$ and $A^2$ independently are unsubstituted amino, amidino or guanidino group, or an optionally substituted 1,2,4-oxadiazol-3-yl or 1,2,4-thiadiazol-3-yl group, R2 is p-hydroxybenzyl, p-methoxybenzyl or hydrogen atom, P is a group of the formula:

—Z—B— in which Z is a group selected from

 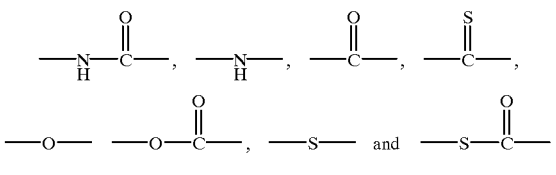

(either of the bonds of them may bonded to B) or a bond, and

B is

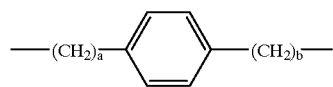

or

—$(CH_2)_c$—

(a and b each is an integer of 0 to 2 (preferably 0 or 1), and c is an integer of 1 to 5) or a bond (excluding the case where Z and B both are a bond), m is an integer of 0 to 2, and n is an integer of 1 to 4.

Furthermore preferable examples of the above-mentioned compounds (Ia) and their salts include compounds (Ia) wherein $A^1$ and $A^2$ independently are unsubstituted amino, amidino or guanidino group, or an optionally substituted 1,2,4-oxadiazol-3-yl or 1,2,4-thiadiazol-3-yl group, $R^2$ is p-hydroxybenzyl, p-methoxybenzyl or hydrogen atom, P is a group of the formula

—Z—B— in which Z is

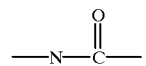

B is

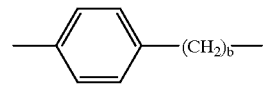

(b is an integer of 0 to 2 (preferably 0 or 1)), m is an integer of 0 to 2, and n is an integer of 1 to 4.

Preferable examples of the compound (I) and their salts include compounds (I) wherein $A^1$ and $A^2$ independently are (1) an amidino or guanidino group optionally substituted with $C_{2-8}$ alkoxycarbonyloxy, (2) an amino group optionally substituted with oxadiazolyl optionally substituted with oxo or $C_{1-4}$ alkyl optionally substituted with halogen, or (3) an oxadiazolyl group optionally substituted with oxo or $C_{1-4}$ alkyl optionally substituted with halogen, D is a group of the formula:

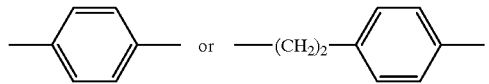

$R^1$ is a hydrogen atom, $R^2$ is a hydrogen atom or a $C_{1-4}$ alkyl group substituted with phenyl optionally substituted with $C_{1-4}$ alkoxy, P is a group of the formula:

—Z—B— wherein Z is a group selected from

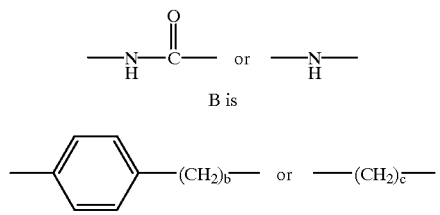

B is

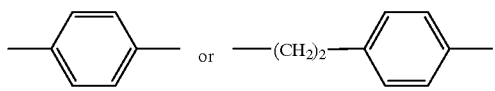

in which b is 0 or 1, and c is an integer of 1 to 5, and n is an integer of 1 to 4.

More preferable examples of the compound (I) and their salts include compounds (I) wherein $A^1$ and $A^2$ are independently
(1) an amidino or guanidino group optionally substituted with methoxycarbonyloxy or
(2) an amino group optionally substituted with 5-oxo-1,2,4-oxadiazol-3-yl or 5-trifluoromethyl-1,2,4-oxadiazol-3-yl, D is

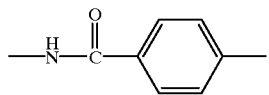

$R^1$ is a hydrogen atom,
$R^2$ is a hydrogen atom or p-methoxybenzyl,
P is

Y is a carboxyl group and
n is 2 or 3.

The compounds of this invention have one or more asymmetric carbons in the molecule, and both R-configurated ones and S-configurated ones relative to these asymmetric carbons are included in the present invention.

Examples of the salts of the compounds (I) and (Ia) of this invention include salt (especially pharmaceutically acceptable salt) such as inorganic acid salts (e.g. hydrochloride, hydrobromide, sulfate, nitrate and phosphate, etc.), organic acid salts (e.g. acetate, tartrate, citrate, fumarate, maleate, toluenesulfonate and methanesulfonate, etc.), metal salts (e.g. sodium salt, potassium salt, calcium salt and aluminum salt, etc.), salts with a base (e.g. triethylamine salt, guanidine salt, ammonium salt, hydrazine salt, quinine salt and cinchonine salt, etc.) and so on.

Specific examples of preferable compounds include 4-(4-amidinobenzoyl)aminoacetyl-3-[3-(4-amidinobenzoyl)aminopropyl]-2-oxopyperazine-1-acetic acid,
4-(4-amidinobenzoyl)aminoacetyl-3-[4-(4-amidinobenzoyl)aminobutyl]-2-oxopiperazine-1-acetic acid,
4-(4-amidinobenzoyl)aminoacetyl-3-[2-(4-amidinobenzoyl)aminoethyl]-2-oxopiperazine-1-acetic acid,
4-(4-amidinobenzoyl)aminoacetyl-3-[2-(4-amidinophenylaminocarbonyl)ethyl]-2-oxopiperazine-1-acetic acid,
4-(4-amidinobenzoyl)aminoacetyl-3-[3-(4-amidinophenylaminocarbonyl)propyl]-2-oxopiperazine-1-acetic acid,
4-(4-amidinobenzoyl)aminoacetyl-3-[4-(4-amidinophenylaminocarbonyl)butyl]-2-oxopiperazine-1-acetic acid,
4-(4-guanidinobenzoyl)aminoacetyl-3-[2-(4-guanidinobenzoylamino)ethyl]-2-oxopiperazine-1-acetic acid,
4-(4-guanidinobenzoyl)aminoacetyl-3-[3-(4-guanidinobenzoylamino)propyl]-2-oxopiperazine-1-acetic acid,
4-(4-guanidinobenzoyl)aminoacetyl-3-[4-(4-guanidinobenzoylamino)butyl]-2-oxopiperazine-1-acetic acid,
4-(4-amidinobenzoylamino)acetyl-3-[2-(4-guanidinobenzoylamino)ethyl]-2-oxopiperazine-1-acetic acid,
4-(4-amidinobenzoylamino)acetyl-3-[3-(4-guanidinobenzoylamino)propyl]-2-oxopiperazine-1-acetic acid,
4-(4-amidinobenzoylamino)acetyl-3-[4-(4-guanidinobenzoylamino)butyl]-2-oxopiperazine-1-acetic acid,
4-[4-(2-aminoethyl)benzoylamino]acetyl-3-[2-(4-amidinobenzoylamino)ethyl]-2-oxopiperazine-1-acetic acid,
4-[4-(2-aminoethyl)benzoylamino]acetyl-3-[3-(4-amidinobenzoylamino)propyl]-2-oxopiperazine-1-acetic acid,
4-[4-(2-aminoethyl)benzoylamino]acetyl-3-[4-(4-amidinobenzoylamino)butyl]-2-oxopiperazine-1-acetic acid,
(S,S)-[3-[3-(4-guanidinobenzoylamino)propyl]-4-[3-(4-methoxyphenyl)-2-[4-(5-trifluoromethyl-[1,2,4]oxadiazol-3-ylamino)benzoylamino]propionyl]-2-oxopiperazin-1-yl]acetic acid,
(S,S)-[4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoylamino]propyl]piperazin-1-yl]acetic acid,
(S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino)benzoylamino]-propyl]piperazin-1-yl]acetic acid or
(S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid, or salts thereof, more preferably, (S)-4-(4-amidinobenzoyl)aminoacetyl-3-{3-(4-amidinobenzoyl)amino}propyl-2-oxopiperazine-1-acetic acid,
(S)-4-(4-guanidinobenzoylamino)acetyl-3-[3-(4-guanidinobenzoylamino)]propyl-2-oxopiperazine-1-acetic acid,
(S)-4-(4-amidinobenzoylamino)acetyl-3-[2-(4-guanidinobenzoylamino)]ethyl-2-oxopiperazine-1-acetic acid,
(S)-4-[4-(2-aminoethyl)benzoylamino]acetyl-3-[3-(4-amidinobenzoylamino)]propyl-2-oxopiperazine-1-acetic acid,
(S,S)-[3-[3-(4-guanidinobenzoylamino)propyl]-4-[3-(4-methoxyphenyl)-2-[4-(5-trifluoromethyl-[1,2,4]oxadiazol-3-ylamino)benzoylamino]propionyl]-2-oxopiperazin-1-yl]acetic acid,
(S,S)-[4-[3-(4-methoxyphenyl)-2-[4-(5-trifluoromethyl[1,2,4]oxadiazol-3-ylamino)benzoylamino]propionyl]-2-oxo-3-[3-[4-(5-trifluoromethyl[1,2,4]oxadiazol-3-ylaminobenzoylamino]propyl]piperazin-1-yl]acetic acid, (S,S)-[4-[3-(4-methoxyphenyl)-2-[4-(5-oxo-4,5-dihydro[1,2,4]oxadiazol-3-ylamino)benzoylamino]propionyl]-2-oxo-3-[4-(5-oxo-4,5-dihydro[1,2,4]oxadiazol-3-ylamino)benzoylamino]-propyl]piperazin-1-yl]acetic acid or (S,S)-4-[2-(4-guanidinobenzoyl)amino-3-(4-methoxyphenyl)propionyl]-3-[3-(4-guanidinobenzoyl)aminopropyl]-2-oxopiperazine-1-acetic acid, or salts thereof, further more preferably, (S)-4-(4-amidinobenzoyl)aminoacetyl-3-{3-(4-amidinobenzoyl)amino}propyl-2-oxopiperazine-1-acetic acid, (S)-4-(4-guanidinobenzoylamino)acetyl-3-[3-(4-guanidinobenzoylamino)]propyl-2-oxopiperazine-1-acetic acid, (S)-4-(4-amidinobenzoylamino)acetyl-3-[2-(4-guanidinobenzoylamino)]ethyl-2-oxopiperazine-1-acetic acid or (S)-4-[4-(2-aminoethyl)benzoylamino]acetyl-3-[3-(4-amidinobenzoylamino)]propyl-2-oxopiperazine-1-acetic acid trifluoroacetate, or salts thereof.

The most preferable example is (S)-4-(4-guanidinobenzoylamino)acetyl-3-[3-(4-guanidinobenzoylamino)]propyl-2-oxopiperazine-1-acetic acid or a salt thereof, more preferably (S)-4-(4-guanidinobenzoylamino)acetyl-3-[3-(4-guanidinobenzoylamino)]propyl-2-oxopiperazine-1-acetic acid or a acid addition salt thereof, further more preferably (S)-4-(4-guanidinobenzoylamino)acetyl-3-[3-(4-guanidinobenzoylamino)]propyl-2-oxopiperazine-1-acetic acid hydrochloride, especially preferably (S)-4-(4-guanidinobenzoylamino)acetyl-3-[3-(4-guanidinobenzoylamino)]propyl-2-oxopiperazine-1-acetic acid dihydrochloride.

And, another preferable example is 4-(4-guanidinobenzoylamino)acetyl-3-[3-(4-guanidinobenzoylamino)]propyl-2-oxopiperazine-1-acetic acid or a salt thereof.

The compounds (I) and (Ia) of this invention can be produced, for example, according to the method described in JP-A-316059/1997. When the compound (I) is obtained in the free form, it can be converted to a salt thereof by a conventional method, and when the compound (I) is obtained as a salt, it can be converted to the compound (I) by a conventional method. Among them, concretely, (S)-4-(4-guanidinobenzoylamino)acetyl-3-[3-(4-guanidinobenzoylamino)]propyl-2-oxopiperazine-1-acetic acid dihydrochloride can be produced by the method mentioned in the Production Example 1 and the like.

The method for transdermal administration of the present invention can be used for treatment or prophylaxis of diseases such as angina pectoris, unstable angina, acute myocardial infarction, Kawasaki disease, acute or chronic heart failure, transient ischemic attack (TIA), cerebral apoplexy, cerebral ischemic disturbance in acute phase of cerebral thrombosis, dissecting aneurysm of the aorta, cerebral vasospasm after subarachnoid hemorrhage, acute or chronic renal disease (e.g. acute or chronic renal disease due to overagglutination such as snake venom and immunopathy), chronic and acute glomerulonephrits, diabetic nephropathy and nerve disturbance, nephrotic syndrome, liver diseases, pulmonary embolism, bronchial asthma, pulmonary edema, adult respiratory distress syndrome (ARDS), arteriosclerotic obliteration, peripheral arterial obstruction, deep vein thrombosis, vibration disease, peripheral obstruction complicated with diabetes mellitus, thrombotic thrombocytopenic purpura (TTP), disseminated intravascular coagulation (DIC), sepsis, surgical or infective shock, postoperative and post-delivery trauma, premature separation of placenta, incompatible blood transfusion, systemic lupus erythematosus, Raynaud's disease, inflammations, arteriosclerosis, hemolytic uremic syndrome, symmetric peripheral necrosis, bedsore and hemorrhoids in mammals including humans (e.g. mouse, rat, guinea pig, dog, rabbit and human). And, the method can be used for preventing thrombosis due to cardiopulmonary bypass surgical operation, surgical operation for pump oxygenator, atrial fibrillation or fracture of hip joint, prosthetic valve replacement, artificial blood vessel and organs, or preventing thrombocytopenia during artificial dialysis, and further for secondary prophylaxis of myocardial infarction. Preventing thrombocytopenia during artificial dialysis also means preventing coagulation or non-washable blood in the shunt of extracorporeal dialysis.

Further, the method for transdermal administration of the present invention can be used for coronary thrombolytic therapy (e.g. enhancing the action of thrombolytic agent such as tissue plasminogen activator (TPA)) and for preventing reobstruction, for preventing reobstruction and restenosis of coronary arteries after PTCA (percutaneous transluminal coronary angioplasty) or stent-indwelling and atherectomy, for preventing reobstruction and restenosis after surgical operation for coronary artery bypass, for preventing ischemic complication (e.g. myocardial infarction, death) after PTCA or coronary thrombolytic therapy, and, besides for inhibiting metastasis of tumors.

The dosage of the active compound for treating or preventing the diseases referred to herein before can vary within a wide range and can, of course, be adjusted to suit the individual circumstances in each particular case. By the present invention, drug administration is safely carried out although the serum drug concentration range between minimum and maximum pharmacologically effective serum concentrations is very small While the dosage varies with the subject diseases, symptoms, subject patients and administration routes, when the compound (I) is administered, by the method for transdermal administration in the present invention, to a patient of unstable angina, or, ischemic complication or reobstruction of coronary or restenosis of coronary after PTCA or coronary thrombolytic therapy, the dosage is an amount where the compound (I) concentration in serum is maintained at preferably about 10 to 500 ng/ml, more preferably about 50 to 300 ng/ml, for an adult (60 kg). By the method for transdermal administration in the present invention, a GP IIb/IIIa antagonist concentration in serum can be reached in the above-mentioned concentration, within preferably about 240 minutes, more preferably in about 120 to 240 minutes, further more preferably in about 120 to 180 minutes, from the initial electric current application step. While the amount of a GP IIb/IIIa antagonist to be added to the porous membrane or the hydrophilic gel in the conductive layer as one (each day) administration, can be selected according to the condition of current administration such as current density or period of a electric current application, when a GP IIb/IIIa antagonist is compound (I), the amount is preferably about 10 to 1000 mg, more preferably about 30 to 1000 mg, further more preferably about 30 to 500 mg.

The rate of absorption of a GP IIb/IIIa antagonist by the method for transdermal administration in the present invention, is preferably about 0.01 to 10 mg/hour, more preferably about 0.1 to 10 mg/hour, further more preferably about 0.2 to 2 mg/hour.

BEST MODE FOR CARRYING OUT THE INVENTION

In the following, the present invention is illustrated specifically by the production example, reference examples and Examples, but these should by no means be construed as limiting the scope of the invention.

Production Example 1

Production of (S)-4-(4-guanidinobenzoylamino)acetyl-3-[3-(4-guanidinobenzoylamino)]propyl-2-oxopiperazine-1-acetic acid dihydrochloride hours. The precipitated crystals were filtered, washed with 89% ethanol 900 ml, air-dried overnight, and vacuum-dried at 50° C. for 9 hours to give crude crystals of Compound (I) 819 g. The crude crystals of Compound (A) was dissolved in water 2.05 L, and to the solution was added active charcoal 16.5 g. The mixture was stirred at room temperature for 30 minutes and filtered. The filtrate was passed through 0.2µ membrane filter, to which was added ethanol 20.5 L. The mixture was stirred at room temperature for 6 hours, and then under ice-cooling for 2 hours. The precipitated crystals were filtered, which were washed with 89% ethanol (1.0 L), vacuum-dried at 50° C. for 9 hours, allowed to stand at RH100% overnight, vacuum-dried at 50° C. for 9 hours, and allowed to stand at RH60–70% for about 3 days to give purified crystals of Compound (A) (dihydrochloride) 753 g.

m.p.: 245–251.5° C.

Elemental Analysis for $C_{27}H_{34}N_{10}O_6 \cdot 2HCl \cdot 1.5H_2O$

Calcd.: C, 46.69; H, 5.66; H, 20.17; Cl, 10.21

Found: C, 46.15; H, 5.62; H, 19.94; Cl, 10.65

Reference Example 1

As the device for transdermal administration by iontophoresis, a device comprising of an anode patch and a cathode patch was prepared.

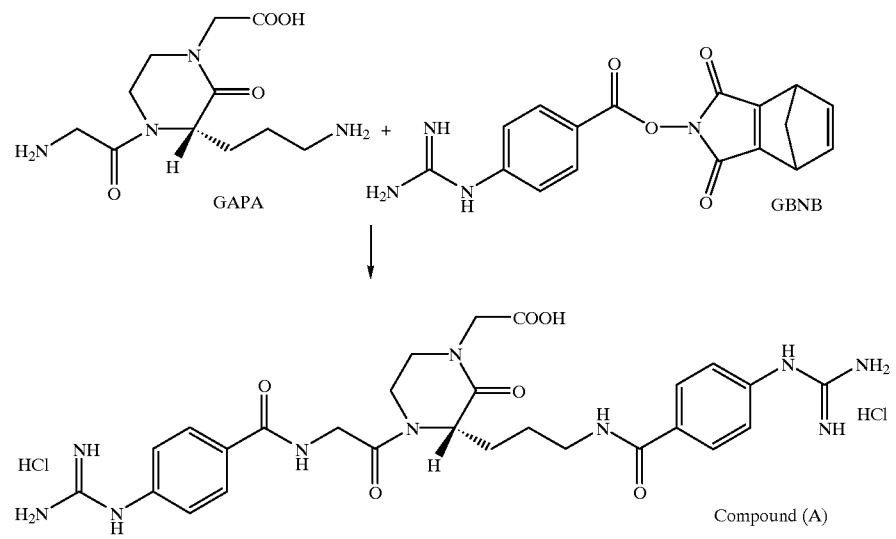

To the solution of (S)-4-glycyl-3-(3-aminopropyl)-2-oxopiperazine-1-acetic acid [GAPA], were added acetonitrile 7.0 L, water 6.6 L and sodium hydrogen carbonate 448 g (5.33 mol), and then N-(4-guanidinobenzoyloxy)-5-norbornene-2,3-dicarboxyimide [GBNB] 1607 g (4.27 mol). The mixture was stirred at room temperature for 4 hours, and the reaction solution was adjusted to pH3 with 2N-HCl and extracted with ethyl acetate (30 L×3). The aqueous layer was concentrated to about 10 L under reduced pressure, and to the residue was added water 10 L. The mixture was adjusted to pH5.0 with sodium bicarbonate, loaded on the resin (SP-207, 30 L-column), washed with pure water 150 L and eluted with 0.003N-HCl/5% acetonitrile 250 L. The desired fractions (about 200 L) were collected and concentrated to about 10 L under reduced pressure. The concentrate was adjusted to pH1.5 with concentrated hydrochloric acid (about 117 ml) and then concentrated to 3 L. To the residue was added ethanol 24 L, and the mixture was stirred at room temperature for 19 hours and then under ice-cooling for 2

As illustrated in FIG. 2, the anode patch comprises a foil silver electrode 1, a conductive layer 2 comprising 1.0% (w/w) of an agar gel containing the about 5% (w/w) ion exchange resin cholestyramine, additives (5% (w/w) of urea, 10% (w/w) of proline, 0.1% (w/w) sodium benzoate, 0.03% (w/w) citric acid) and a thickener(0.25% (w/w) of xanthan gum and 0.25% (w/w) of locust bean gum), a cup-shaped support 3 (inner diameter: about 30 mm, thickness: about 1.5 mm, volume: about 1.3 mL, weight: about 1.3 g) for holding 1 and 2, an adhesive member 4 for affixing the device in position on the skin, and a porous membrane (drug-holding membrane) 5 for holding the drug [Hydrophilic Durapore (TM), Nippon Millipore]. The area of contact surface of the anode patch with the skin is about 9 cm².

The cathode patch was comprising a print silver/silver chloride electrode and 10% PVA gel.

The animals to which the drug was administered were 7-week-old male SD rats. The skin of the dorsal part of each rat was shaved, and to that part, the iontophoretic device comprising the anode patch including a drug holding membrane carrying 29 μg of the compound synthesized in Production Example 1 and the cathode patch not containing said compound was affixed to the shaved skin site. Then the device was connected with the electric generator (50 kHz, 50% duty). Iontophoretic transdermal administration (transdermal permeation) was performed by imposing the constant transport current (0.1 mA/cm2) for 60 minutes. The blood samples were taken periodically following the start of the administration. The serum concentrations of the compound were determined by enzyme immunoassay.

Reference Example 2

Except that 609 μg of the compound synthesized in Production Example was applied to the drug-holding membrane, the transdermal administration of the compound by iontophoresis and serial determination of its serum concentration were carried out in otherwise the same manner as in Reference Example 1.

Reference Example 3

Except that 2494 μg of the compound synthesized in Production Example 1 was applied to the drug-holding membrane, the transdermal administration of the compound by iontophoresis and serial determination of its serum concentration were carried out in otherwise the same manner as in Reference Example 1.

The time course of the serum concentration of the compound synthesized in Production Example 1 following the commencement of administration in each of Reference Examples 1 to 3 is presented in FIG. 3. The results indicated that current-responsive blood concentrations were obtained. As shown in FIG. 3, the compound was absorbed through the skin in relation to the electrical current applied, resulting in an increasing serum concentration of the compound. Furthermore, the absorption by the iontophoresis of the compound was dose-dependent.

Reference Example 4

In place of the agar gel of the conductive layer 2 used in Reference Example 1, 1% (w/w) agarose gel was used. This gel contained the compound obtained in Production Example 1 at the concentration of 4.32% (w/w) (absolute amount: 56.13 mg), cholestyramine-OH at the concentration of 5% (w/w), and L-prolineat the concentration of 10% (w/w). Furthermore, in place of the drug-holding porous membrane 5, a porous membrane (Hydrophilic Durapore, Japan Millipore Co. Ltd.) not containing the drug was used. The area of the skin-contacting surface of this porous membrane was about 17.3 cm$^2$. Thus the prepared device was the same as that obtained in Reference Example 1 except for the changes with the conductive layer 2 and the porous membrane 5.

The animals to which the above-mentioned compound was administered were beagle dogs weighing about 15 kg. The skin of the dorsal part of each dog was shaved, and to that part, the above-mentioned iontophoretic device was affixed. Then the device was connected with the electric generator (50 kHz; 50% duty). Iontophoretic transdermal administration (transdermal permeation) was performed by imposing the constant transport current (current density: 0.05 mA/cm$^2$) for 24 hours. By considering the consumption of the cathod electrode during the current imposition, the cathod patch was replaced with a new one every 4 hours. Blood samples were taken periodically following the start of the administration. The serum concentrations of the compound were determined by the enzyme immunoassay.

Figure 4:
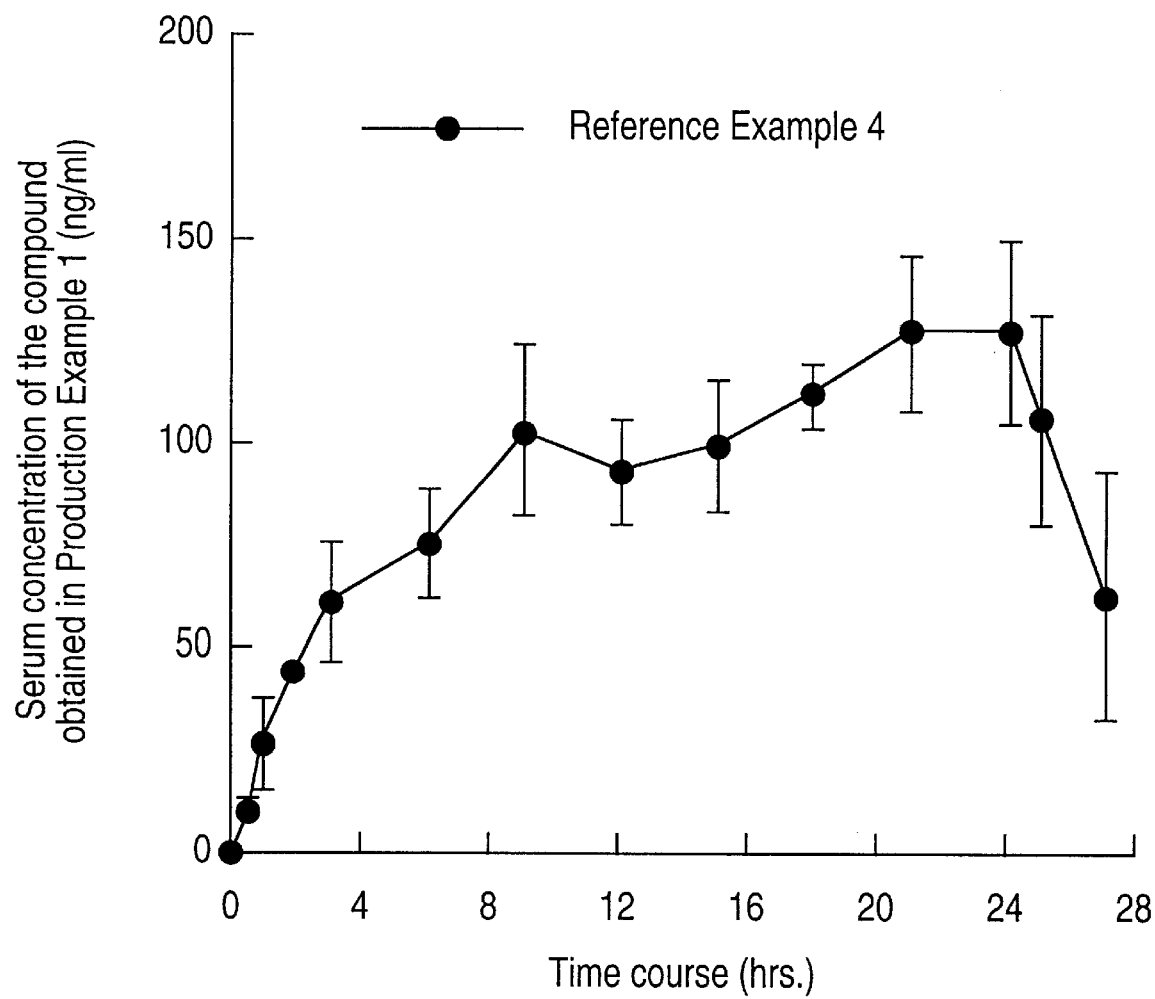
FIG. 4. is a graph illustrating the change of the serum concentration of the compound obtained in Production Example 1 as time passed in Reference Example 4, wherein -●- shows the serum concentration of Reference Example 4.

The time course of the serum concentration of the compound obtained in Production Example 1 following the start of the administration is shown in FIG. 4. The administration resulted in a current-responding serum-drug-level profile. As shown in FIG. 4, the compound was transdermally absorbed by the systemic circulation constantly throughout the current imposition for 24 hours. The serum concentration of the compound reached a high level around 8 hours and thereafter the level was maintained until the end of the administration. By the comparison of this serum drug level with the steady-state serum-drug level when the same compound was intravenously infused at a constant rate, the rate of absorption of this compound was estimated to be approximately 1 mg/hr.

EXAMPLE 1

Except that the compound synthesized in Production Example 1 was applied to the drug-holding membrane in an amount of 609 μg and the under-mentioned current application conditions were used, the transdermal administration of the compound by iontophoresis and serial determination of its serum concentration were carried out in otherwise the same manner as in Reference Example 1.

The electrical current application was carried out in two consecutive steps using a current density of 0.1 mA/cm2 up to 45 minutes, viz. the initial current application step, and a current density of 0.05 mA/cm$^2$ from 45 minutes through 255 minutes, viz. the second current application step.

EXAMPLE 2

Except that the compound synthesized in Production Example 1 was applied to the drug-holding membrane in an amount of 609 μg and the under-mentioned current application conditions were used, the transdermal administration of the compound by iontophoresis and serial determination of its serum concentration were carried out in otherwise the same manner as in Reference Example 1.

The electrical current application was carried out in two steps using a current density of 0.1 mA/cm$^2$ up to 15 minutes, viz. the initial current application step, and a current density of 0.025 mA/cm$^2$ from 15 minutes through 585 minutes, viz. the second current application step.

EXAMPLE 3

Except that the compound synthesized in Production Example 1 was applied to the drug-holding membrane in an amount of 1218 μg and the under-mentioned current application conditions were used, the transdermal administration of the compound by iontophoresis and serial determination of its serum concentration were carried out in otherwise the same manner as in Reference Example 1.

The electrical current application was carried out in two steps using a current density of 0.1 mA/cm$^2$ up to 15 minutes, viz. the initial current application step, and a current density of 0.025 mA/cm$^2$ from 15 minutes through 585 minutes, viz. the second current application step.

Figure 5:
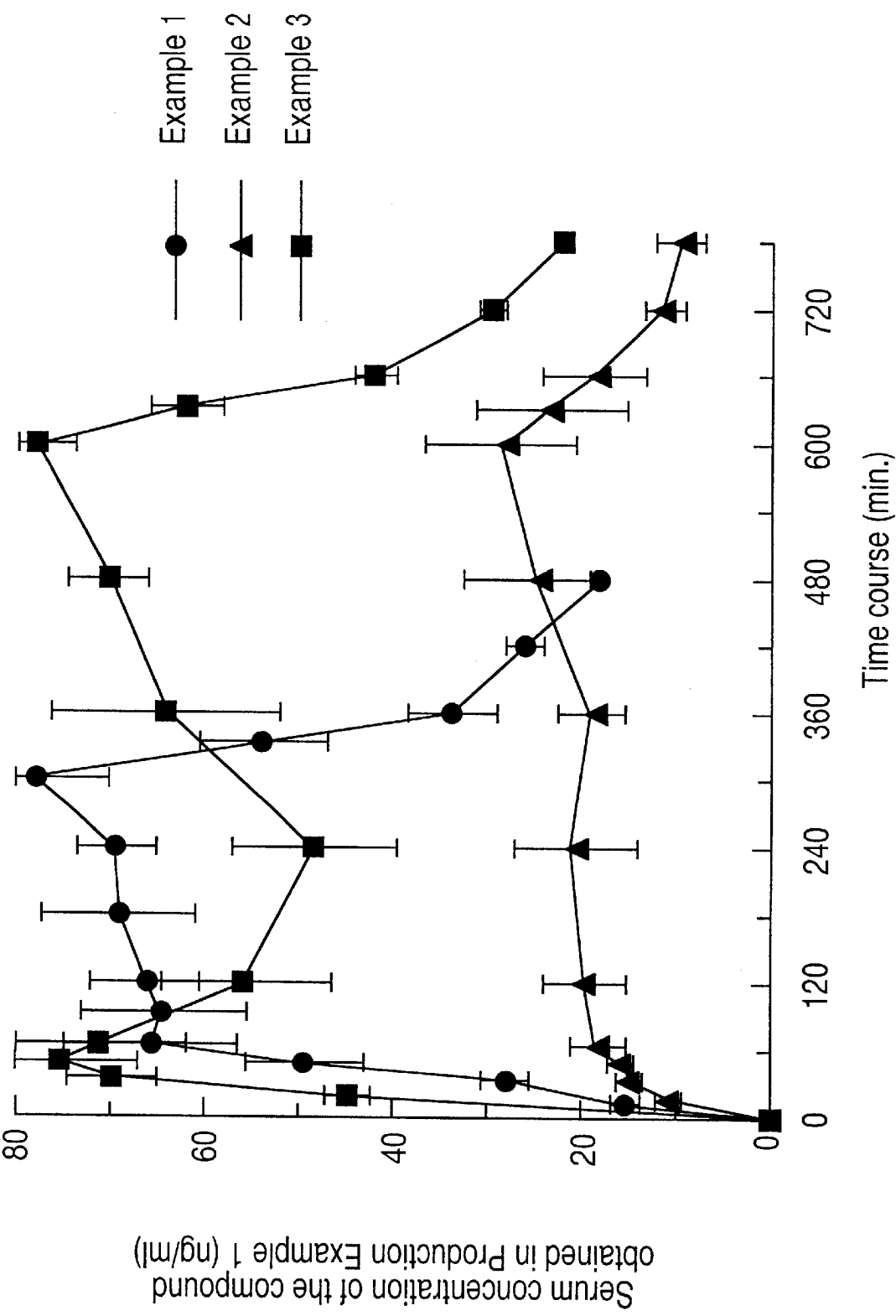
FIG. 5. is a graph illustrating the change of the serum concentration of the compound obtained in Production Example 1 as time passed in Examples 1, 2 and 3, wherein -●- shows the serum concentration of Example 1, -▲- shows the serum concentration of Example 2, -■- shows the serum concentration of Example 3.

The time course of the serum concentration of the compound synthesized in Production Example 1 following the transdermal administration of the compound by iontophoresis in each of Examples 1 to 3 is presented in FIG. 5.

It is apparent from FIG. 5 that under the conditions of any of Examples 1 to 3, current application-responsive absorption of the compound over a long period of time was obtained and a steady-state serum level could be achieved just like administration by intravenous drip. Comparison of Example 1 with Example 2 showed that the steady-state serum concentration was proportional to the current density. On the other hand, comparison of Example 2 with Example 3 showed that the steady-state serum concentration of the compound was proportional to the dosage or amount of application. Therefore, although the current density in the second current application step in Example 3 was half of that in Example 1, the two-fold dose used in Example 3 as compared with Example 1 resulted in substantially the same steady-state serum concentration.

INDUSTRIAL APPLICABILITY

A method for transdermal administration by iontophoresis of the present invention does not substantially injure or stimulate the skin and a GP IIb/IIIa antagonist concentration in serum can reach its pharmacologically effective range shortly after the beginning of its administration, since in the method of the present invention, an electric current application is performed under specific conditions. Further, such blood concentration is maintained almost at the same level for a long duration. Therefore, the GP IIb/IIIa antagonist is efficiently administered transdermally by the present invention and its serum concentration is controlled to be maintained in the pharmacologically effective range, but not to reach the adverse-effect range, so that, its superior pharmacological efficacy is achieved.

What is claimed is:

1. A method for transdermal administration of a GP IIb/IIIa antagonist by iontophoresis, which comprises:

conducting a first series of electric current application steps, and then conducting a further or second series of electric current application step(s) for maintaining a pharmacologically effective GP IIb/IIIa antagonist concentration in the serum, wherein the first series comprises plural electric current application steps which are conducted continuously without interval, in which each step comprises the steps of:

providing a GP IIb/IIIa antagonist to the skin, and
      applying electric currents to drive the antagonist into the skin, in which the current density is progressively reduced in the subsequent application step, wherein the further or second series comprises one or more electric current application step(s) which are preceded by an interval before each application, and wherein the antagonist concentration in the serum is maintained at about 10 to 500 ng/ml within 240 minutes from the initial electric current application step in the first series of application steps.

2. The method according to claim 1, which comprises two electric current application steps, progressively reduced in current density.

3. The method according to claim 1, wherein the current density of the initial electric current application step is about 0.005 to 0.5 mA/cm$^2$.

4. The method according to claim 1, wherein the period of the initial electric current application step is about 1 to 240 minutes.

5. The method according to claim 1, wherein the current density of the last electric current application step is about 10 to 80% of that of the initial electric current application step.

6. The method according to claim 1, wherein the period of the last electric current application step is about 1 minute to about 72 hours.

7. The method according to claim 1, wherein a GP IIb/IIIa antagonist is a compound of the formula

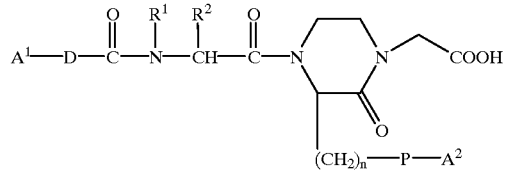

wherein $A^1$ and $A^2$ independently are a proton-accepting group;

D is a spacer having a 2- to 6-atom chain optionally bonded through a hetero-atom and/or a 5- or 6-membered ring which is, depending on its bonding position, counted as 2- or 3-atom chain;

$R^1$ is a hydrogen atom or a hydrocarbon group;

$R^2$ is a hydrogen atom or a residual group formed by removing —CH(NH$_2$)COOH from an α-amino acid, or $R^1$ and $R^2$ may be combined to form a 5- or 6-membered ring;

P is a spacer having a 1- to 10-atom chain optionally bonded through a hetero-atom and/or a 5- or 6-membered ring, provided that the 5- or 6-membered ring is, depending on its bonding position, counted as 2- or 3-atom chain;

and n is an integer of 0 to 8, or a salt thereof.

8. The method according to claim 7, wherein $A^1$ and $A^2$ are independently an unsubstituted amino, amidino or guanidino group.

9. The method according to claim 7, wherein R1 is hydrogen atom.

10. The method according to claim 1, wherein a GP IIb/IIIa antagonist is (S)-4-(4-guanidinobenzoylamino) acetyl-3-[3-(4-guanidinobenzoylamino)propyl]-2-oxopiperazine-1-acetic acid or a salt thereof.

11. The method according to claim 1, wherein the absorption rate of the GP IIb/IIIa antagonist is about 0.01 to 50 mg/hour.

12. The method according to claim 1, wherein the further series comprises about 2 to 99 subsequent electric current applications.

13. The method according to claim 1, wherein the current density of the further series of electric current applications is substantially the same as that of the last application step of the first series of electric current applications.

14. The method according to claim 1, wherein the interval of non-electric current application is about 0.1 to 120 minutes.

* * * * *